US006987105B2

(12) United States Patent
Bazan et al.

(10) Patent No.: US 6,987,105 B2
(45) Date of Patent: Jan. 17, 2006

(54) SYNTHESIS AND USE OF THIENOTRIAZOLODIAZEPINES

(75) Inventors: Nicholas G. Bazan, New Orleans, LA (US); Julio Alvarez Builla Gomez, Madrid (ES)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 10/258,343

(22) PCT Filed: Apr. 26, 2001

(86) PCT No.: PCT/US01/13496

§ 371 (c)(1),
(2), (4) Date: Mar. 10, 2003

(87) PCT Pub. No.: WO01/83440

PCT Pub. Date: Nov. 8, 2001

(65) Prior Publication Data

US 2003/0229078 A1 Dec. 11, 2003

Related U.S. Application Data

(60) Provisional application No. 60/200,420, filed on Apr. 28, 2000.

(51) Int. Cl.
*A61P 27/02* (2006.01)

(52) U.S. Cl. .................................................. 514/218

(58) Field of Classification Search ................ 514/218; 540/555
See application file for complete search history.

(56) References Cited

U.S. PATENT DOCUMENTS

| 5,049,559 A | 9/1991 | Braquet et al. ............. 514/219 |
| 5,049,560 A | 9/1991 | Esanu et al. ................ 514/219 |
| 5,492,906 A * | 2/1996 | Braquet et al. ............. 514/219 |

FOREIGN PATENT DOCUMENTS

| EP | 0 369 810 | 5/1990 |
| FR | 2 779 652 | * 12/1999 |

OTHER PUBLICATIONS

Doly et al. (Ophthalmic Research (1993), 25(5), 314–18).*
Doly et al. (Acta Ophthalmologica Scandinavica (1995), 73(2), 155–7).*
Menerath et al. (Journal of Ocular Pharmacology and Therapeutics (1997), 13(1), 81–88).*
Baker M.L. et al., "Differential effect of platelet–activating factor on adhesion molecule expression by astrocytes and microglia," Abstract, Soc. Neurosci., vol. 22 (1996).

Bazan, H. et al., "Platelet–activating factor induces collagenase expression in corneal epithelial cells," Proc. Natl Acad Sci, vol. 90, pp. 8678–8682 (1993).
Bazan, H. et al., "Platelet–activating factor induces cyclooxygenase–2 gene expression in corneal epithelium. Requirement of calcium in the signal transduction pathway," Invest Ophthalmol & Vis Sci, vol. 38, No. 12, pp. 2492–2501 (1997).
Bazan N.G., "Bioactive lipid and neuronal plasticity in neurodegenerative diseases," Abstract, 655th Meeting of Biochemical Society, University of Manchester, Manchester, England (1995).
Bazan, N.G., "Bioactive lipids and gene expression in neuronal plasticity," Chapter 3, *Molecular and Cellular Mechanisms of Neuronal plasticity*, Ehrlich (ed), Plenum Press, NY, pp. 37–49 (1998).
Bazan, N.G. "Bioactive lipids in the modulation of excitatory amino acid neurotransmitter release and of gene expression," Abstract, Satellite Meeting of 15th ISN, "Lipid Messengers in the Nerous System, " Tokyo, Japan (1995).
Bazan, N.G., "Cell signaling and gene expression in photoreceptor survival," Abstract, Ocular Cell and Molecular Biology Symposium, Keystone, CO (1999).

(Continued)

*Primary Examiner*—Bruck Kifle
(74) *Attorney, Agent, or Firm*—Bonnie J. Davis; John H. Runnels

(57) ABSTRACT

A new method to synthesize the platelet-activating factor antagonist which is a derivative of thienotriazolodiazepene, tetrahydro-4,7,8,10 methyl-1(chloro-2 phenyl)-6 (methosy-4 phenyl carbamoyl)-9 pyrido[4,3-:4,5] thieno[3, 2-f] triazolo-1,2,4 [4,3-α] diazepine-1,4] (1) is disclosed. The compound synethesized by this new method has been designated "LAU-8080" which has the same structure as the compound currently named in the literature as "BN-50730." LAU-8080 was shown to prevent photoreceptor cell death, inhibit pathological neovascularization in the retina, and minimize the loss of neurons due to ischemic-reperfusion damage due to stroke. Thus LAU-8080 can be used to treat the retinal diseases of age-related macular degeneration, retinitis pigmentosa, and diabetic retinopathy. It can also be used to minimize the neuronal damage due to stroke.

(1)

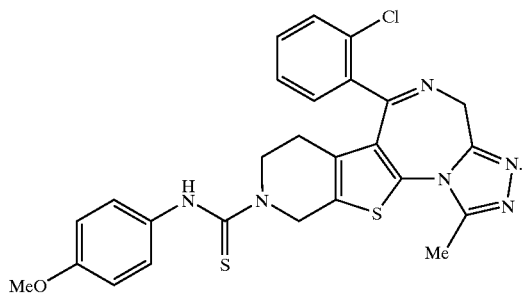

1 Claim, 6 Drawing Sheets

OTHER PUBLICATIONS

Bazan, N.G., "COX–2 and oxidative stress in ischemic brain injury and neurodegeneration," Abstract, 5th IUBMB Conference on The Biochemistry of Health and Diseases, Jersalem, Israel (1998).

Bazan, N.G., "COX–2 in ischemic brain injury and in neurodegeneration," Abstract, Second International Workshop on COX–2, Kapalua, Hawaii (1998).

Bazan, N.G., "COX–2 in synaptic plasticity and neurodegenerative diseases," Abstract, First International Workshop on COX–2, New Orleans, LA (1997).

Bazan, N.G., "COX–2 in synaptic plasticity and neurodegenration," Abstract, IBCs Industry Symposium on COX–2 Inhibitiors, San Diego, CA (1998).

Bazan, N.G., "Endogenous neuroprotection mechanisms and inflammatory signaling in stroke," Abstract, Princeton Conference on Cerebrovascular Disease (1998).

Bazan, N.G., "Epileptogenesis: Significance of information flow, sprouting and neuronal damage," Abstract, Merritt–Putnam, Lectures on Epilepsy, New Orleans, LA (1998).

Bazan, N.G., "Excitable membrane–derived injury mediators: Glutamate release and regulation of gene expression," Abstract, XVth Washington International Spring Symposium, Neurodegenerative Diseases, 95, Molecular and Cellular Mechanisms, and Therapeutic Advances, Advances, Washington, DC (1995).

Bazan, N.G., "Inflammatory signaling pathways in pharmacology of cerebral ischemia," *Pharmacology of Cerebral Ischemia,* J Krieglstein (ed.) Medpharm Scientific Publ, Stuttgart, pp. 173–180 (1996).

Bazan, N.G., "Inflammatory signaling pathways in phamacology of cerebral ischemia," *Pharmacology of Cerebral Ischemia,* J Krieglstein (ed.) Medpharm Scientific Publ, Stuttgart, pp. 173–180 (1996).

Bazan, N.G., "Inflammatory signaling pathways in pharmacology of cerebral ischemia," 6th International Symposium on Pharmacology of Cerebral Ischemia, Marburg, Germany (1996).

Bazan, N.G., "Injury messengers, transcription factors, and gene expression in status epilepticus," Summary, Int'l Symposium on Status Epilepticus Mechanisms and Management, Santa Monica, CA (1997).

Bazan, N.G., "Lipid messengers and prostaglandin endoperoxide synthase–2 in neuronal cell death," *Primer on Cerebrovascular Diseases,* Chapter 53, Welsh et al. (eds.), Academic Press, pp. 193–195 (1997).

Bazan, N.G., "Lipid messengers in synaptic signaling: significance in neuronal survival," Abstract, Satellite of the Joint meeting of the 16th Biennial meeting of the International Society for Neurochemistry and the 28th Annual Meeting of the American Society for Neurochemistry, "Lipid Messengers in the Nervous System," New Orleans, LA (1997).

Bazan, N.G., "Lipid–derived second messengers in the regulation of gene expression," Abstract, The Advanced School of Neurochemistry 2nd Biennial Course on From Signal Transduction to Gene Expression, Okasaki, Japan (1995).

Bazan, N.G., "Neuronal cell signal transduction and gene expression in response to injury and experimental epilepsy," Abstract, Fifth International Symposium MSNR 91, New Frontiers in the Biochemistry and Biophysics of Stroke, Neurotrauma and Other Neurological Disorders, Bristol, England (1991).

Braquet, p. et al., "New trends in PAF anatagonist research: A new series of potent hetrapazine–derived PAF antagonists," Agents and Actions, vol. 32, pp. 34–36 (1991).

Campbell, F.Z. et al., "Excitatory amino acid neurotransmitter receptor agonist and platelet–activating factor (PAF) enhance the expression of the inducible proastagladin synthase–2 (COX–2) in primary hippocampal neurons," Satellite of the meeting of the 16th Biennial meeting of the international Society for Neurochemistry and the 28th Annual Meeting of the American Society for Neurochemistry, "Lipid Messengers in the Nervous System," New Orleans, LA (1997).

Decoster, M.A. et al., "Platelet–activating factor modulates intracellular calcium dynamics in rat hippocampai neurons," Joint Meeting of the American Society for Biochemistry and Molecular Biology, Am. Soc. for Investigative Pathology, New Orleans, LA (1996).

DeCoster, M.A. et al., "Platelet–activating factor is a downstream messenger of kainate–induced activation of mitogen–activated protein kinases in primary hippocampal neurons," J Neurosci Res. vol. 53, pp. 297–303 (1998).

de la Cruz, J.P. et al., "Effect of WEB 2086–BS, an antagonist of platelet–activating factor receptors, on retinal vascularity in diabetic rats," European Journal of Pharmacology, vol. 360, pp. 37–42 (1998).

Doly, M. et al., "Prevention of chloroquine–induced electroretinographic damage by a new platelet–activating factor antagonist, BN 50730," Opthalmic REs, vol. 25, pp. 314–318 (1993).

Doly, M. et al., "Protective effect of a specific PAF antagonist on vincristine–induced experimental retinopathy," ACTA Opthalmologica Scandinavica, pp. 155–157 (1995).

Doucet, J.P., "Excitable membranes, lipid messengers, and immediate–early genes: Alteration of signal transduction in neurodulation and neurotrauma," Mol Neurobiol, vol. 6, No. 4, pp. 407–424 (1992).

Doucet, J.P. et al., "Muscarinic induction of zif/268 immediate–early gene in NG108–15 cells in mediated by platelet–activating factor," Abstract, FASEB J, vol. 7, No. 4, p. A184 (1993).

Doucet, J.P. et al., "Triazolobenzodiazepine–based antagonism of platelet–activating factor and induction of Fos expression in human SH–SY5Y neurobastoma cells," Abstract, Soc Neurosci, vol. 17, p. 170 (1991).

Feuerstein, G.Z. et al., Symposium, "Lipid Mediators in Synaptic Transduction of Neuronal Cells: Physiological and Pathological Implications," Abstract, Soc Neurosci, vol. 17, p. 1470 (1991).

Gershanik, E.F. et al., "Antagonist of the Intracellular Platelet–activating Factor (PAF) Receptor Protects Photoreceptors from Light Damage," IOVS Abstract Issue, vol. 41, No. 4, ARVO Annual Meeting, Fort Lauderdale, Florida 5 (2000).

Gordon, W.C. et al., "Retinal COX–2 induction by light preceeds photoreceptor cell death," Abstract, International Symposium "New Targets in Inflammation: Inhibitors of COX–2 or Adhesion Molecules," New Orleans, Louisiana (1996).

Harris, T. et al., "Light–induced prostaglandin endoperoxide synthase–2 (COX–2) expression is selectively concentrated in inner segments of rod photoreceptors," Abstract, Invest Ophthalmol & Vis Sci. Suppl., vol. 38, No. 4 (1997).

Izquierdo, I. et al., "Memory enhancement by intrahippocampl, intraamygdala or intraentorhinal infusion of platelet–activating factor measured in an inhibitory avoidance task," Proc Natl Acad Sci USA, vol. 92, pp. 5047–5051 (1995).

Jerusalinsky, D. et al., "Effect of antagonists of platelet–activating factor receptors on memory of inhibitory avoidance in rats," Behav and Neural Biol, vol. 62, pp. 1–3 (1994).

Kato, K. et al., "Platelet activating factor as a potential retrograde messenger in CA1 hippocampal long–term potentiation," Nature, vol. 367, pp. 175–179 (1994).

Lehmann, J., "Research in Vision and Opthalmology," Meeting Report, Highlights of ARVO Meeting, Sarasota, FL, pp. 441–444 (1993).

Lukiw, W.J. et al., "DNA–binding proteins at the promotor of the inducible TIS10/PGS–2 gene modified by seizures or ischemia in the hippocampus," Abstract, Epilepsia, vol. 35, No. 8, p. 43 (1994).

Lukiw, W.J. et al., "Human COX–2 promoter modulators," International Symposium, "New Targets in Inflammation: Inhibitors of COX–2 or Adhesion Molecules," New Orleans, Louisiana (1996).

Lukiw, W.J. et al., "Protein–DNA interactions in the promoter of the cyclooxygenase (COX2) primary response element in NG108–15 cells in rat and human brain," Abstract, Soc Neurosci $25^{th}$ Annual Meeting, San Diego, CA (1995).

Lukiw, W.J. et al., "Protein–DNA interactions in the proximal promoter of the inducible cyclooxygenase (COX–2) gene in hippocampus during experimental epilepsy and brain damage," Abstract, XV Washington Int'l Spring Symposium, Neurodegenerative Diseases 95: Molecular and Cellular Mechanisms, and Therapeutic Advances, Washington, DC (1995).

MacLennan, K.M. et al., "Platelet–activating factor in the CNS," Progress in Neurobiology, vol. 50, pp. 585–596 (1996).

Marcheselli, V.I. et al., "Seizures promote a rapid transcriptional upregulation of PGHS–2 in rat hippocampus, which inhibited by the PAF receptor antagonist BN 50730," Abstract, $26^{th}$ Annual Meeting, Soc Neurosci, vol. 22, p. 1439, Washington, DC (1996).

Marcheselli, V.L., "Platelet–activating factor is a messenger in the electroconvulsive shock–induced transcriptional activation of c–fos and zif–268 in hippocampus," J of Neuroscience Res. vol. 37, pp. 54–61 (1994).

Marcheselli, V.L. et al., "Distinct platelet–activating factor binding sites in synaptic endings and intracellular membranes of rat cerebral cortex," J of Biological Chem, vol. 265, No. 16, pp. 9140–9145 (1990).

Marcheselli, V.L. et al., "A PAF antagonist of dexamethasone inhibits the seizure–triggered sustained upregulation of the inducible prostaglandin synthase in the hippocampus," Abstract, Soc for Neurosci, vol. 20, No. 433.9 (1994).

Marcheselli, V.L. et al., "A specific antagonist for intracellular platelet–activating factor (PAF) binding sites lacks activity on synaptic membranes," Abstract, Trans Amer Soc Neurochem, vol. 22, p. 187 (1991).

Marcheselli, V.L. et al., "ECS–induced zif–268 in hippocampus is inhibited by a PAF antagonist," Abstract, Trans Amer Soc Neurochem, vol. 23, p. 255 (1992).

Marcheselli, V.L. et al., "Enhanced expression of the inducible prostaglandin synthase gene precedes light–induced photoreceptor apoptosis," Second Annual Vision Research Conference, "Retinal Development, Degeneration and Function Restitution," Fort Lauderdale, FL (1998).

Marcheselli, V.L. et al., "Inducible prostaglandin synthase and zif–268 mRNA upregulation in vasogenic cerebral edema: Inhibition by a PAF antagonist," Abstract, Soc Neurosci, vol. 21, p. 1867 (1995).

Marcheselli, V.L. et al., "Intracellular platelet–activating factor binding sites and immediate–early gene expression in hippocampus during seizures," $14^{th}$ ISN Meeting, J. Neurochem., vol. 61, Suppl., –Montpellier, France (1993).

Marcheselli, V.L. et al., "Light damage induced photoreceptor apoptosis involves a PAF receptor mediated signaling pathway which involves upregulation of COX–2 and BCL–2," Abstract, J Neurohem, vol. 72, Suppl, p. S50(D) (1999).

Marcheselli, V.L. et al., "Neuroprotection by BN–50730 in the Stroke Model of Mouse Middle Cerebral Artery Occlusion," Soc. for Neuroscience Abstracts, vol. 26, No. 1–2: $30^{th}$ Annual Meeting of the Soc. of Neuroscience, New Orleans, LA (2000).

Marcheselli, V.L. et al., "Partial inhibition of ischemia–reperfusion induced COX–2 gene expression is associated with neuroprotection in a model of MCAO," Abstract, $4^{th}$ Int'l Workshop, "Maturation Phenomenon in Cerebral Ischemia Apoptosis and/or Necrosis, Neuronal Recovery vs. Death, and Protection for Infarction," New Orleans, LA (1999).

Marcheselli, V.L. et al., "Platelet activating factor (PAF) enhances glutamic acid release in the retina through a presynaptic receptor," Abstract, Invest Ophthalmol Vis Sci, vol. 34, No. 4, p. 1048 (1993).

Marcheselli, V.L. et al., "Platelet–activating factor (PAF), kainic or glutamate increase expression of the inducible prostaglandin H synthase–2 (COX–2) in primary hippocampal neurons," Abstract, Experimental Biology, New Orleans, LA (1997).

Marcheselli, V.L. et al., "Platelet–activating factor (PAF) stimulates glutamic acid release from hippocampal synatosomes," Abstract, Soc Neurosci, vol. 23, p. 1779, No. 729.15 (1993).

Marcheselli, V.L. et al., "Platelet–activating factor is a mediator of fos expression induced by a single seizure in rat hippocampus," Abstract, Soc Neurosci, vol. 17, p. 349 (1991).

Marcheselli, V.L. et al., "Platelet–activating factor presynaptic receptor activation induces glutamic acid release in the retina, a mechanism associated with retinal damage," Abstract, $33^{rd}$ Annual Meeting, Am. Soc. Cell Biology, New Orleans, LA (1993).

Marcheselli, V.L. et al., "Prostaglanin D synthase is rapidly translocated from the retinal pigment epithelium into the interphotorecptor matrix, vitreous, and aqueous humor," Abstract, Joint Meeting Am. Soc. for Biochem. and Mol. Biol. & Am. Soc. for Inves. Path., New Orleans, LA (1996).

Marcheselli, V.L. et al., "Significance of COX–2 in neuronal and photoreceptor survival," Abstract, Satellite of Joint meeting of 16th Biennial meeting of Int'l Soc. for Neurochem & 28th Annual Meeting of the Am. Soc. for Neurochem., "Lipid Messengers in the Nervous Systems," New Orleans, LA (1997).

Marcheselli, V.L. et al., "Sustained induction of prostaglandin endoperoxide synthase–2 by seizures in hippocampus: Inhibition by a platelet–activating factor antagonist," J Biol Chem, vol. 271, No. 40, pp. 24794–24799 (1994).

Marcheselli, V.L. et al., "Sustained upregulation of inducible prostaglandin synthase expression in hippocampus by a single seizure: Inhibition by a PAF antagonist," Abstract, Epilepsia, vol. 35, No. 8, p. 138 (1994).

Marcheselli, V.L. et al., "Transcriptional upregulation of COX–2 in hippocampus by seizures," Abstract, Int'l Symp, "New Targets in Inflammation: Inhibitors of COX–2 or Adhesion Molecules," New Orleans, Louisiana (1996).

Marcheselli, V.L. et al., "Platelet–activating factor is a messenger in the electroconvulsive shock–induced transcriptional activation of c–fos and zif–268 in hippocampus," J Neurosci Res, vol. 37, 1, pp. 54–61 (1994).

Menerath, J.M. et al., "Experimental Electroretinographic Exploration of Retinal Ischemia: Preventive Use of Free Radical Scavengers and Anti–PAF Agents," J. Ocul. Pharmacol. Ther., vol. 13, No. 1, pp. 81–88 (1997).

Millerin M. et al., "Prevention of inherited retinal dystrophy by a specific PAF antagonist, BN50730," Abstract (1992).

Moises, J. et al., "A PAF antagonist inhibits the expression of hippocampal immediate early genes in a kindling model of epilepsy," Abstract, Epilepsia, vol. 35, No. 8, p. 139 (1994).

Moises, J.P. et al., "Brain injury induces COX–2 expression: Inhibition by a PAF antagonist," Abstract, $17^{th}$ Annual Nat'l Neurotrauma Society meeting, Miami, FL (1999).

Mukherjee, P. et al., "Kainic acid–induced epileptogenesis increases mitogen activated protein kinase activity in hippocampus: Involvement of platelet–activating factor as a mediator," Abstract, Epilepsia, vol. 36, Suppl. 4, p. 26 (1995).

Mukherjee, P. et al., "PAF Induction of human COX–2 gene," Abstract, Int'l symposium, "New Targets in Inflammation: Inhibitors of COX–2 or Adhesion Molecules," New Orleans, Louisana (1996).

Mukherjee, P. et al., "Platelet–activating factor is a messenger in kainate epileptogenesis–enhanced mitogen activated protein kinase activity in hippocampus," Abstract, Soc Neurosci, vol. 21, p. 1475 (1995).

Mukherjee, P.K. et al., "Cell specific activation of zif/268 promotor by platelet–activating facto in transfected NG108–15 and SH–SY5Y cells," Abstract, FASEB J, vol. 7, No. 4, p. A470 (1993).

Mukherjee, P.K. et al., "Differential activation of p38, JNK, and mitogen–activated protein kinases (MAPKs) by platelet–activating factor (PAF), glutamate (GLU), and kainate (KA) in primary hippocampul neurons," Abstract, Experimental Biology, New Orleans, LA (1997).

Mukherjee, P.K. et al., "Glutamate receptor signaling interplay modulates stress–sensitive mitogen–activated protein kinases and neuronal cell death," J Biol Chem, vol. 274, pp. 6493–6498 (1999).

Mukherjee, P.K. et al., "Platelet–activating factor (PAF) induces the expression of vascular endothelial growth factor (VEGF)," Abstract, Invest Opthalmol & Vis Sci, vol. 38, p. S357 (1997).

Mukherjee, P.K. et al., "Platelet–activating factor (PAF) or kainate (KA) activation of p–38, JNK–1, and mitogen–activated protein kinase (MAPKs) follow different pathways than glutamate (GLU) in primary hippocampal Neurons," Abstract, Satellite of Joint meeting of 16th Biennial meeting of Int'l Soc. for neurochem. . . . , "Lipid Messengers in the Nervous System," New Orleans, LA (1997).

Mukherjee, P.K. et al., "Platelet–activating factor (PAF) or kainate (KA) activation of P–38, JNK–1, and mitogen–activated protein kinases (MAPKs) follow different pathways than glutamate (GLU) in primiary hippocampal neurons," Abstract, Satellite of Joint meeting of 16th Biennial meeting of the Int'l Soc. for Neurochem . . . , "Stroke, Nuerotrauma and Other Neurological Diseases," New Orleans, LA (1997).

Pires, A.L.A. et al., "Long–lasting inhibitory activity of the hetrazepinic BN–50730 on exudation and cellular alterations evoked by PAF and LPS," Br.J. Pharmacol., vol. 113, pp. 994–1000 (1994).

Rodriguez de Truco, E.B. et al., "The onset of light damage selectively induces the early response gene inducible cycloxygenase in the rat retina," Abstract, Joint Meeting of Am. Soc. for Biochem. and Molecular Biology and . . . , New Orleans, LA (1996).

Serou, M. et al., "A Secretory phospholipase $A_2$ ($sPLA_2$) receptor agonist induces expression of prostaglandin endoperoxide synthase–2 (COX–2) in primary cortical neurons but not glial cultures," Abstract, Satellite of Joint meeting of 16th Biennial meeting of Int'l Soc. for Neurochem.and . . . , "Lipid Messengers in the Nervous Systems," New Orleans, LA (1997).

Serou, M. et al., "Interleukin–1 beta activates expression of cyclooxygenase–2 and inducible nitric oxide synthase in priamry hippocampal neuronal culture: Platelet–activating factor as a preferential mediator of cyclooxygenase–2 expression," J Neurosci Res, vol. 58, pp. 593–598 (1999).

Silva, C.L. et al.. "Formation of a highly stable complex between BN–50730 [tetrahydro–4,7,8,10 methyl–1 (chloro–2 phenyl–6 (methoxy–4 phenyl–carbamoyl)–9 pyrido [4', 3'–4,5]thieno [3,2–f ]triazolo–1,2,4 [4,3–a]diazepine–1, 4]and the platelet–activating factor receptor in rabbit platelet membranes," Biochemical Pharmacology, vol. 51, pp. 193–196 (1996).

Tao, Y. et al., "COX–2 gene expression and $Ca^{2+}$influx in corneal epithelial cells," Abstract, Int'l Symposium, "New Targets in Inflammation: Inhibitors of COX–2 or Adhesion Molecules," New Orleans, Louisana (1996).

Tao, Y. et al., "Platelet–activating factor enhances urokinase–type plasminogen activator (uPA) gene expression in corneal epithelium," Invest Ophthalmol Vis Sci, vol. 37, No. 10, pp. 2037–2046 (1996).

Tao, Y. et al., "Platelet–activating factor induces the expression of metalloproteinases–1 and –9 but not –2 or –3 in the corneal epithelium," Invest Opthalmol Vis Sci, vol. 36, No. 2, pp. 345–354 (1995).

Teather, L.A. et al., "Effects of intrahippocampal injections of platelet–activating factor and the PAF antagonists BN 52021 and BN 50730 on spatial memory in rats," Abstract, Satellite of Joint meeting of 16th Biennial meeting of Int'l Soc. for Neurochem. and . . . , "Lipid Messengers in the Nervous System," New Orleans, LA (1997).

Teather, L.A. et al., "Effects of posttraining intrahippocampal injections of platelet–activating factor and PAF antagonists on memory," Neurobiol of Learning and Memory, vol. 70, pp. 349–363 (1998).

Teather, L.A. et al., "Immunocytochemical localization of cyclooxygenase–2 (COX–2) in rat brain following kainic acid–induced status epilepticus," Abstract, FASEB J, vol. 12, No. 5, p. A750 (1998).

Tian, X. et al., "Platelet–activating factor receptor–deficient mice show meuroprotection after transient focal cerebral ischemia," Abstract (2000).

Wang, J.–H et al., "Inhibition of cytokine action of PAF antagonists in immortalized astrocytes," Abstract, Soc. Neurosci, vol. 24, p. 1540 (1998).

* cited by examiner

SYNTHESIS AND USE OF THIENOTRIAZOLODIAZEPINES

This is the United States national stage of International Application PCT/US01/13496, filed Apr. 26, 2001, which claims the priority filing date of U.S. provisional application 60/200,420, filed Apr. 28, 2000 under 35 U.S.C. §119(e).

TECHNICAL FIELD

This invention pertains to a new method of synthesizing a derivative of thienotriazolodiazepene [tetrahydro-4,7,8,10 methyl-1(chloro-2 phenyl)-6 (methoxy-4 phenyl-carbamoyl)-9 pyrido[4',3'-4,5]thieno[3,2-f]triazolo-1,2,4[4,3-a] diazepine-1,4] and to new methods of using this compound therapeutically to treat age-related macular degeneration, retinitis pigmentosa, diabetic retinopathy, and stroke related neuronal damage.

BACKGROUND ART

U.S. Pat. No. 5,492,906 discloses synthesis and use of several derivatives of thieno-triazolo-diazepine, including tetrahydro-4,7,8,10 methyl-1(chloro-2 phenyl)-6 (methoxy-4 phenyl-carbamoyl)-9 pyrido[4',3'-4,5]thieno[3,2-f]triazolo-1,2,4[4,3-a] diazepine-1,4. However, the syntheis is different from that reported below.

The derivative of thienotriazolodiazepene of interest when synthesized by the method disclosed in U.S. Pat. No. 5,492,906 has been described in the literature as a platelet-activiating factor antagonist and named BN-50730.

Age-related macular degeneration involves a complex pathophysiology characterized by photoreceptor cell death and in some cases also pathological neovascularization.

Retinitis Pigmentosa is an inherited form of retinal degeneration that has been linked to mutations in several genes. Blindness occurs due to the selective death of photoreceptor cells.

Diabetic retinopathy involves pathological neovascularization that leads to functional impairments in the retina and eventually to retinal detachment.

Platelet-activating factor (PAF; 1-O-alkyl-2-acetyl-sn-glycero-3-phosphocholine) is a membrane-derived second messenger that is a potent mediator of inflammatory, ischemic, and immunological responses. PAF is rapidly produced in tissues in response to injury and other forms of stimulation. See N. G. Bazan et al., "A Platelet-activating factor and retinoic acid synergistically activate the inducible prostaglandin synthase gene," Proc. Natl. Acad. Sci. USA, vol. 91, pp. 5252–5256 (1994). Intracellular and cell surface binding sites for PAF have been identified and distinguished by using diverse PAF antagonists that show a preference for one or more of the binding sites. See V. L. Marcheselli et al., "A Distinct platelet-activating factor binding sites in synaptic endings and intracellular membranes of rat cerebral cortex," Journal of Biological Chemistry, vol. 265, pp. 9140–9145 (1990). Two binding sites found were associated with microsomal intracellular membranes and a third binding site was associated with the synaptosomal membrane (the extracellular plasma membrane). One of the internal microsomal binding sites displays the highest known affinity for PAF.

Several PAF antagonists have been identified. Most of the antagonists are competitive in nature. The antagonists can be divided into three distinct groups: PAF-related compounds such as CV 3988; synthetic PAF-unrelated compounds such as WEB 2086 and SR 27417; and natural products including BN-52021. See A. L. A. Pires et al., "A Long-lasting inhibitory activity of the hetrazepinic BN-50730 on exudation and cellular alterations evoked by PAF and LPS," Br. J. Pharmacol., vol. 113, pp. 994–1000 (1994). A unique PAF antagonist, BN-50730, a hetrazepine, is known to displace PAF from microsomal membranes, but not from the synaptosomal, plasma membrane. See V. L. Marcheselli and N. G. Bazan, "A Platelet-activating factor is a messenger in the electroconvulsive shock-induced transcriptional activation of c-fos and zif-268 in hippocampus," Journal of Neuroscience Research. vol. 37, pp. 54–61 (1994). Moreover, BN-50730 and WEB 2086, another PAF antagonist, are known to have different dissociation kinetics. See C. L. Silva et al., "A Formation of a highly stable complex between BN-50730 [tetrahydro-4,7,8,10 methyl-1 (chloro-2 phenyl)-6 (methoxy-4 phenyl-carbamoyl)-9 pyrido[4',3'-4,5]thieno[3,2-f]triazolo-1,2,4[4,3-a]diazepine-1,4] and the platelet-activating factor receptor in rabbit platelet membranes," Biochemical Pharmacology, vol. 51, pp. 193–196 (1996).

DISCLOSURE OF INVENTION

We have discovered a new method to synthesize the platelet-activating factor antagonist which is a derivative of thienotriazolodiazepene, tetrahydro-4,7,8,10 methyl-1 (chloro-2 phenyl)-6 (methosy-4 phenyl carbamoyl)-9 pyrido [4',3-:4,5]thieno[3,2-f] triazolo-1,2,4[4,3-α] diazepine-1,4). We have named the compound synethesized by this new method "LAU-8080" which has the same structure as the compound currently named in the literature as "BN-50730." LAU-8080 was shown to prevent photoreceptor cell death, inhibit pathological neovascularization in the eye, and minimize the loss of neurons due to ischemic-reperfusion damage due to stroke. Thus LAU-8080 can be used to treat the retinal diseases of age-related macular degeneration, retinitis pigmentosa, and diabetic retinopathy. It can also be used to minimize the neuronal damage due to stroke.

MODES FOR CARRYING OUT THE INVENTION

EXAMPLE 1

Figure 1:
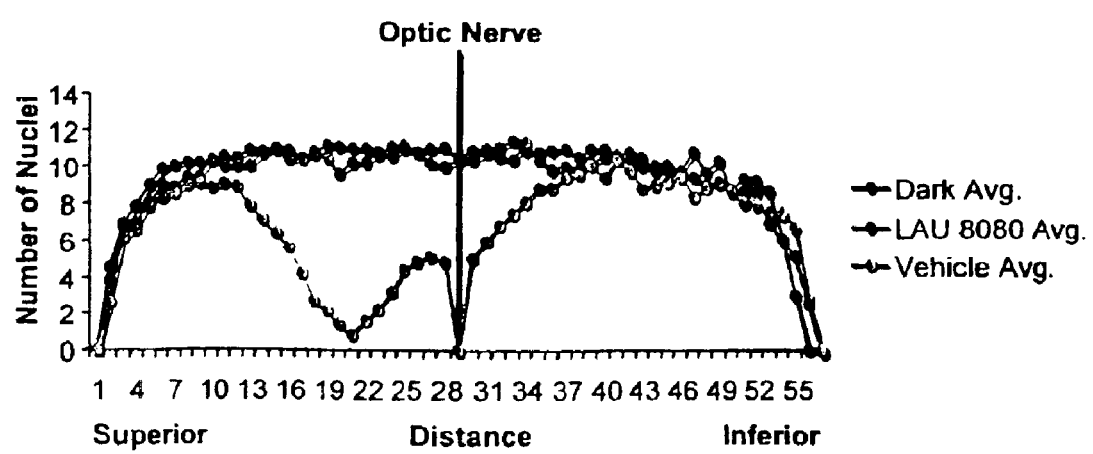
FIG. 1 illustrates the average number of photoreceptor nuclei across the retina when exposed to only dark (Dark Avg.), to bright light and LAU-8080 (LAU-8080 Avg.), and to bright light and control vehicle (Vehicle Avg.).

Synthesis of LA U-8080.

In the diagram below appears the synthetic route to obtain the target compound 1.

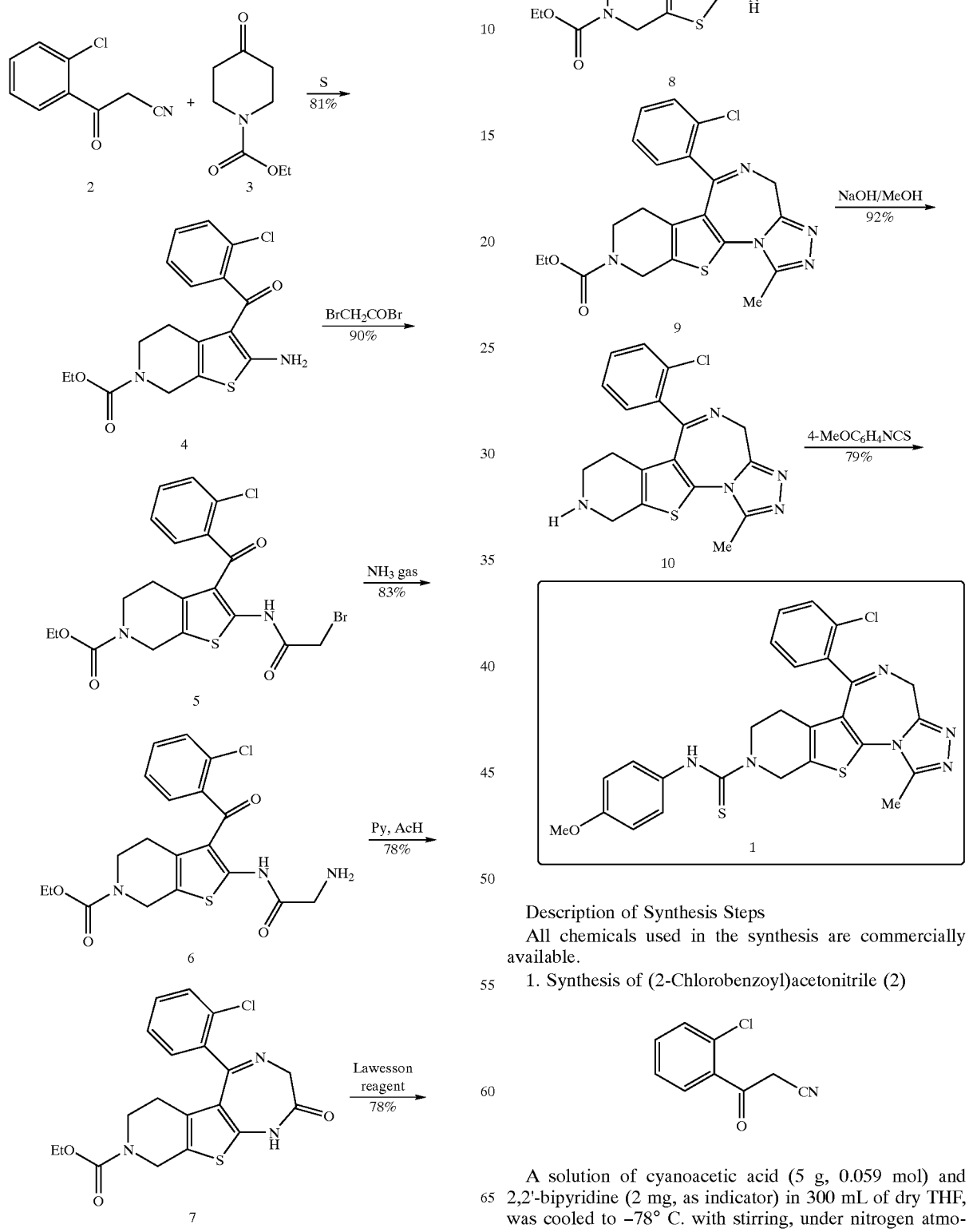

Description of Synthesis Steps

All chemicals used in the synthesis are commercially available.

1. Synthesis of (2-Chlorobenzoyl)acetonitrile (2)

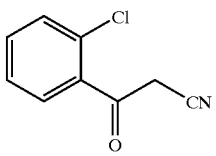

A solution of cyanoacetic acid (5 g, 0.059 mol) and 2,2'-bipyridine (2 mg, as indicator) in 300 mL of dry THF, was cooled to −78° C. with stirring, under nitrogen atmosphere. To this mixture, n-BuLi, 1.6 M in hexane (73 mL, 0.116 mol) was dropwise added, allowing the reaction temperature to slowly rise to 0° C.

When the red color persisted at 0° C., the slurry was recooled to −70° C. and then, (2-chloro)benzoyl chloride (5.14 g, 0.029 mol) in 50 mL of dry THF was dropwise added. The slurry was stirred at −70° C. for 1 hour, and then allowed to rise to room temperature.

Then, hydrochloric acid 1N (100 mL) was added to the mixture, which was extracted with EtOAc (3×75 mL), and the combined organic extracts were washed with saturated sodium hydrogen carbonate solution (2×75 mL) and brine (2×75 mL). The organic layer was then dried over sodium sulfate, filtered and evaporated under reduced pressure to give a residue which was purified by silica gel chromatography. Elution with hex/EtOAc (7:3) gave the title compound as a yellow solid (4.06 g, 77%). M.p. 56–58° C. (EtOH)

IR (KBr): 2961, 2210, 1709, 1590, 1433, 1320, 1251, 1053 cm$^{-1}$. $^{1}$H NMR (CDCl$_3$, 300 MHz) δ: 7.62 (d, 1H, J=7.8 Hz), 7.50–7.39 (m, 3H), 4.14 (s,2H) ppm. Analysis, calculated for C$_9$H$_6$ClNO (179.61 g/mol)

|  | % C | % H | % N |
|---|---|---|---|
| Calculated | 60.19 | 3.37 | 7.80 |
| Found | 60.63 | 3.53 | 7.63 |

2. Synthesis of 2-Amino-3-(2-chlorobenzoyl)-6-ethoxycarbonyl-4,5,6,7-tetrahydropyrido[3,4-b] thiophene (4)

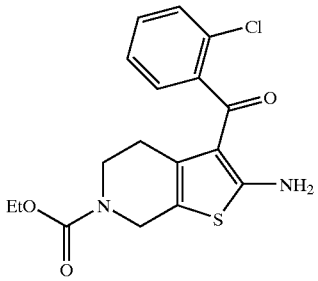

A mixture of 32 g (0.178 mol) of 2-chlorobenzoylacetonitrile, 30.5 g (0.178 mol) of N-ethoxycarbonyl-4-piperidone, 6.8 g (0.21 mol) of powdered sulfur and 15.65 mL (0.178 mol) of morpholine in 190 mL of MeOH, was refluxed for 2 hours. Then, the mixture was cooled and the precipitate was filtered off and washed with diethyl ether, to yield the product as a yellow solid (43 g).

The filtrated liquids were concentrated, and the residue was chromatographed using hexane/EtOAc (8:2) as eluent, to obtain an additional crop of 12 g of 4. The total amount of the product was 55 g, (81%) as a pale yellow solid, after recrystallization from MeOH. M.p. 194–195° C. (yellow prisms, MeOH)

IR (KBr):3259, 2983, 1679, 1578, 1432, 1298, 1270, 1233, 1117 cm$^{-1}$. $^{1}$H NMR (CDCl$_3$, 300 MHz) δ: 7.42–7.20 (m, 4H), 4.37 (bt., 2H, J=2.0 Hz), 4.13 (q, 2H, J=7.1 Hz); 3.41 (bt, 2H, J=5.8 Hz), 1.80–1.74 (m, 2H), 1.25 (t, 3H, J=7.1 Hz) ppm. $^{13}$C NMR (CDCl$_3$, 50 MHz) δ: 188.9, 174.2, 167.0, 155.3, 141.2, 130.3, 130.1, 129.7, 127.7, 126.9, 114.3, 112.9, 61.6, 42.6, 40.8, 25.9, 14.6 ppm. Analysis Calculated for C$_{17}$H$_{17}$ClN$_2$O$_3$S (364.85 g/mol)

|  | % C | % H | % N |
|---|---|---|---|
| Calculated | 55.96 | 4.70 | 7.68 |
| Found | 55.62 | 4.64 | 7.56 |

3. Synthesis of 2-Bromoacetamido-3-(2-chlorobenzoyl)-6-ethoxycarbonyl-4,5,6,7-tetrahydro pyrido[3,4-b] thiophene (5)

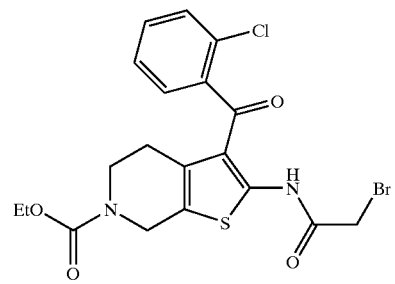

To a solution of 50 g (0.137 mol) of 4 in 800 mL of CH$_2$Cl$_2$ at 0° C., 30.48 g (0.15 mol, 13.25 mL) of bromoacetyl bromide were dropwise added. The reaction mixture was stirred overnight at room temperature. Then, the mixture was poured over 500 mL of ice-water and extracted with CH$_2$Cl$_2$. The combined organic extracts were dried over Na$_2$SO$_4$, and evaporated under reduced pressure.

The residue was poured into cold EtOH-Et$_2$O and the title compound precipitated as a yellow solid, that was filtered and washed with a mixture EtOH-diethyl ether (48 g were isolated). The filtrated liquids were evaporated and the remaining oil was chromatographed in a silica gel column using CH$_2$Cl$_2$ as eluent, to give an additional crop of 12 g of the product. The total amount of 5 was 60 g (90%) as a pale yellow solid. M.p. 84–86° C. (EtOH)

IR (KBr): 2927, 1707, 1693, 1680, 1622, 1520, 1431, 1231 cm$^1$. $^{1}$H NMR (CDCl$_3$, 300 MHz) δ: 12.88 (bs., 1H, NH), 7.45–7.28 (m, 4H), 4.56–4.53 (m, 2H), 4.15 (q, 2H, J=7.0 Hz), 4.13 (s, 2H), 3.46 (bt., 2H, J=5.7 Hz), 1.91–1.87 (m, 2H), 1.26 (t, 3H, J=7.0 Hz) ppm. Analysis Calculated for C$_{19}$H$_{18}$BrClN$_2$O$_4$S (485.79 g/mol)

|  | % C | % H | % N |
|---|---|---|---|
| Calculated | 46.98 | 3.73 | 5.77 |
| Found | 46.92 | 3.84 | 5.64 |

4. Synthesis of 3-Aminoacetamido-3-(2-chlorobenzoyl)-6-ethoxycarbonyl-4,5,6,7-tetrahydropyrido[3,4-b]thiophene (6)

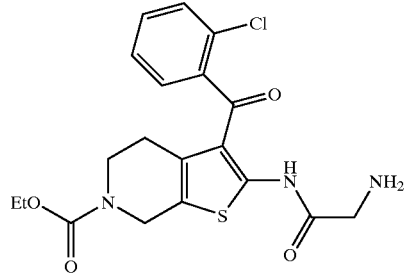

To a solution of 50 g (0.103 mol) of 5 in 800 mL of dry THF, at 0° C., NH$_3$ gas was added for 12 hours. Then, the solvent was evaporated and EtOAc (500 mL) was added.

The organic layer was washed with water and brine (3×100 mL), dried over soudium sulphate and evaporated under reduced pressure. The crude was purified by silica gel chromatography using EtOAc as eluent, to yield the title compound 6 (36 g, 83%) as a white-yellow solid. M.p. 95–97° C. (EtOH)

IR (KBr): 3330, 2935, 1692, 1618, 1501, 1434, 1232, 1082 cm$^{-1}$. $^1$H NMR (CDCl$_3$, 300 MHz) δ: 13.07 (bs, 1H),7.42–7.31 (m, 4H), 4.54–4.51 (m, 2H), 4.14 (q, 2H, J=6.9 Hz), 3.66 (s, 2H), 3.44 (bt., 2H, J=5.8 Hz), 1.90–1.87 (m, 2H), 1.25 (t, 3H, J=6.9 Hz) ppm. $^{13}$C NMR (CDCl$_3$, 50 MHz) δ: 191.2, 178.5, 171.9, 155.3, 150.6, 140.5, 131.0, 130.2, 130.0, 127.7, 127.1, 120.3, 112.9, 61.6, 44.8, 42.6, 40.8, 25.5, 14.6 ppm. Analysis calculated for C$_{19}$H$_{20}$ClN$_3$O$_4$S (421.91 g/mol)

|  | % C | % H | % N |
|---|---|---|---|
| Calculated | 54.09 | 4.78 | 9.96 |
| Found | 54.38 | 4.91 | 9.22 |

5. Synthesis of 5-(2-chlorophenyl)-8-ethtoxycarbonyl-6,7,8,9-tetrahydro-3H-pyrido[4',3':4,5] thieno[3,2-f]-1,4-diazepine-2-one (7)

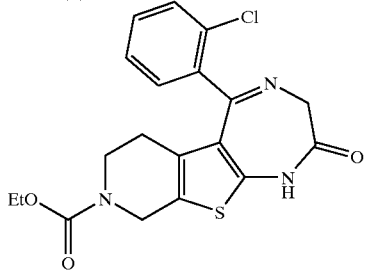

A solution of 30 g (0.071 mol) of 6 in a mixture of pyridine (93 mL), AcOH (30 mL) and toluene (560 mL) was heated under reflux with a Dean-Stark apparatus for 5 hours. Then, the solvents were evaporated under reduced pressure and the crude was chromatographed using hexane/EtOAc (1:1) as eluent to obtain 22.4 g (78%) of 7 as a white solid. m.p. 209–210° C. (CH$_3$CN)

$^1$H NMR (CDCl$_3$, 300 MHz) δ: 7.50–7.34 (m, 4H), 4.53 (s, 2H), 4.41–4.38 (m, 2H), 4.14 (q, 2H, J=7.2 Hz), 3.48–3.44 (m, 2H), 1.83–1.78 (m, 2H), 1.24 (t, 3H, J=7.2 Hz) ppm. MS (m/z, rel. int.): 405 (8), 403 (M$^+$, 19), 376 (36), 374 (100), 348 (9), 346 (23), 302 (9), 239 (14). Analysis Calculated for C$_{19}$H$_{18}$ClN$_3$O$_3$S (403.89 g/mol)

|  | % C | % H | % N |
|---|---|---|---|
| Calculated | 56.50 | 4.49 | 10.40 |
| Found | 56.23 | 4.55 | 10.17 |

6. Synthesis of 5-(2.chlorophenyl)-8-ethoxycarbonyl-6,7,8,9-tetrahydro-3H-pyrido[4',3':4,5]-thieno[3,2-f]-1,4-diazepine-2-thione (8).

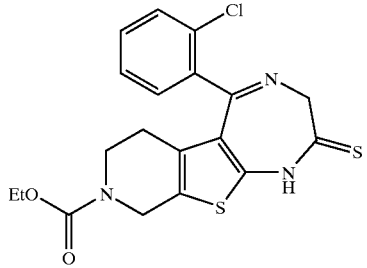

To a solution of 21 g (0.052 mol) of 7 in 175 mL of dimethoxyethane at 90° C., 12.6 g (0.031 mol) of Lawesson reagent were added. The mixture was stirred at the same temperature for 2 hours, then, it was cooled, the solvent removed under vacuum and the residue was purified by chromatography using as eluent CH$_2$Cl$_2$/acetone (9.5:0.5 to 9:1) to yield the title compound as a yellowish solid (18 g, 78%). M.p. 236–237° C. (white yellowish powder, CH$_3$CN)

IR (KBr) 3155, 2982, 1692, 1593, 1564, 1481, 1433, 1352, 1233 cm$^{-1}$. $^1$H NMR (CDCl$_3$, 300 MHz) δ: 11.00 (bs., 1H), 7.42–7.32 (m, 4H), 4.80–4.76 (m, 2H), 4.54 (s, 2H), 4.15 (q, 2H, J=7.1 Hz), 3.47–3.44 (m, 2H), 1.83–1.80 (m, 2H), 1.26 (t, 3H, J=7.1 Hz) ppm $^{13}$C NMR (CDCl$_3$, 50 MHz) δ: 196.2, 165.4, 155.3, 144.7, 137.1, 133.0, 131.2, 131.1, 130.0, 128.0, 127.1, 126.0, 64.4, 61.9, 42.6, 40.6, 25.3, 14.6 ppm. MS (m/z, rel. int.): 419 (M$^+$, 29), 392 (42), 391 (22), 390 (100), 346 (15), 283 (13), 237 (5), 149 (8). Analysis Calculated for C$_{19}$H$_{18}$ClN$_3$O$_2$S$_2$ (419.96 g/mol)

|  | % C | % H | % N |
|---|---|---|---|
| Calculated | 54.34 | 4.32 | 10.01 |
| Found | 54.57 | 4.33 | 9.84 |

7. Synthesis of 6-(2-chlorophenyl)-9-ethoxycarbonyl-1-methyl-7,8,9,10-tetrahydro-4H-pyrid-[4',3':4,5]thieno[3,2-f]-1,2,4-triazolo[4,3-a]-1,4-diazepine (9).

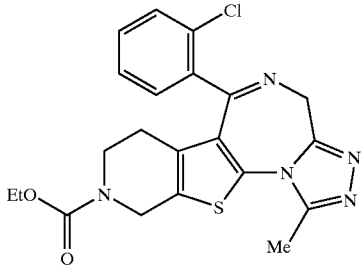

A mixture of the thioamide 8 (18 g, 0.0429 mol) and acetyl hydrazine (3.81 g, 0.051 mol) in 220 mL of dioxane was heated at 130° C. for 8 hours. Then, the dioxane was evaporated, and the residue was purified by chromatography (CH$_2$Cl$_2$/MeOH 9.5:0.5) to obtain 9 as a yellow solid (14 g, 74%). M.p. 234–235° C. (yellowish prisms. CH$_3$CN)

IR (KBr): 2982, 1698, 1604, 1468, 1414, 1233, 1117 cm$^{-1}$. $^1$H NMR (CDCl$_3$, 300 MHz) δ: 7.42–7.31 (m, 4H), 5.59 (d, 1H, J=11.0 Hz), 4.85 (d, 1H, J=16.6 Hz), 4.44 (d, 1H, J=16.6 Hz), 4.22–4.19 (m, 1H), 4.14 (q, 2H, J=7.0 Hz), 3.90–3.87 (m, 1H), 3.19–3.14 (m, 1H), 2.67 (s, 3H), 2.04–2.01 (m, 1H), 1.79–1.73 (m, 1H), 1.24 (t, 3H, J=7.0 Hz) ppm. $^{13}$C NMR (CDCl$_3$, 50 MHz) δ: 164.5, 155.1, 153.5, 149.5, 137.4, 134.3, 132.5, 131.3, 131.1, 130.9, 130.1, 128.9, 127.2, 112.8, 61.8, 46.9, 42.6, 40.5, 25.3, 14.5, 11.9 ppm. MS (m/z, rel. int.): 443 (3), 441 (M$^+$,10), 414 (39), 412 (100), 329 (9), 327 (21), 302 (5), 300 (15), 264 (17), 237 (19) ppm. Analysis Calculated for C$_{21}$H$_{20}$ClN$_5$O$_2$S (441.94 g/mol)

|  | % C | % H | % C |
|---|---|---|---|
| Calculated | 57.07 | 4.56 | 15.85 |
| Found | 56.96 | 4.61 | 15.63 |

8. Synthesis of 6-(2-chlorophenyl)-1-methyl-7,8,9,10-tetrahydro-4H-pyrido[4'3':4,5]thieno[3,2-f]-1,2,4-triazolo[4,3-a]-1,4-diazepine (10).

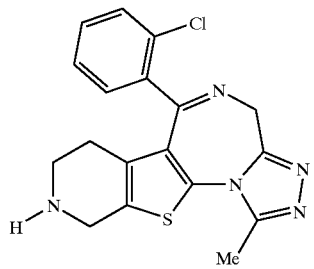

A solution of 9 (14 g, 0.0317 mol) in MeOH (100 mL) and 4N NaOH (90 mL) was heated at 90° C. overnight. The mixture was diluted with brine and extracted with EtOAc (3×100 mL). The organic phase was dried over sodium sulphate, and evaporated under reduced pressure to yield the compound 10 as a white solid (10.7 g, 92%). M.p. 196–198° C. (acetone)

IR (KBr): 2932, 1603, 1542, 1496, 1415, 1379, 1324, 1084, 1034 cm$^{-1}$. $^1$H NMR (CDCl$_3$, 300 MHz) δ: 7.44–7.29 (m, 4H), 5.57 (d, 1H, J=12.3 Hz), 4.19 (d, 1H, J=12.3 Hz), 4.01 (s, 2H), 3.00–2.97 (m, 1H), 2.82–2.80 (m, 1H), 2.67 (s, 3H), 2.02–1.99 (m, 1H), 1.65–1.62 (m, 1H) ppm. $^{13}$C NMR (CDCl$_3$, 50 MHz) δ: 164.8, 153.6, 149.5, 137.7, 132.5, 131.7, 131.5, 130.9, 130.8, 129.4, 127.1, 112.8, 46.9, 44.3, 42.6, 26.3, 12.0 ppm. MS (m/z, rel. int.): 371 (24), 369 (M$^+$, 66), 340 (12), 306 (20), 305 (100), 265 (25), 264 (85), 237 (41), 235 (33), 137 (58) ppm. Analysis Calculated for C$_{18}$H$_{16}$ClN$_5$S (369.88 g/mol)

|  | % C | % H | % N |
|---|---|---|---|
| Calculated | 58.45 | 4.36 | 18.93 |
| Found | 58.55 | 4.04 | 18.64 |

9. Synthesis of LAU-8080 (6-(2-chlorophenyl)-9-[(4-methoxyphenyl)thiocarbamoyl]-1-methyl-7,8,9,10-tetrahydro-4H-pyrido[4',3':4,5]thieno[3,2-f]-1,2,4-triazolo[4,3-a]-1,4-diazepine (1)).

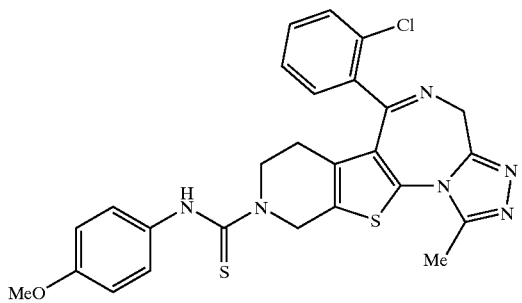

To a suspension of 5 g (0.0135 mol) of the amine 10 in 60 mL of toluene 2.23 g (13.5 mmol) of 4-methoxyphenyl isothiocianate were dropwise added. The mixture was stirred at room temperature for 3 hours and the white precipitate that appeared was filtered off and washed with toluene and diethyl ether. The solid was recrystallized from acetone to give 5.75 g (79%) of the title compound as a white powder. M.p.: 184–187° C. (acetone)

IR (KBr): 3232, 1603, 1511, 1415, 1241, 1206, 1033 cm$^1$. $^1$H NMR (CDCl$_3$, 300 MHz) δ: 7.53 (bs, 1H, NH), 7.44–7.28 (m, 4H), 7.07 (d, 2H, J=8.8 Hz), 6.84 (d, 2H, J=8.8 Hz), 5.57 (d, 1H, J=13.3 Hz), 5.24 (d, 1H, J=15.3 Hz), 4.78 (d, 1H, J=15.3 Hz), 4.28–4.18 (m, 2H), 3.80 (s, 3H), 3.60–3.49 (m, 1H), 2.64 (s, 3H), 2.20–2.12 (m, 1H), 1.80–1.70 (m, 1H) ppm. $^{13}$C NMR (CDCl$_3$, 50 MHz) δ: 183.9, 164.4, 157.7, 153.5, 149.6, 137.2, 134.5, 132.6, 132.4, 131.7, 131.3, 130.9, 130.2, 128.8, 128.6, 127.3, 126.5, 114.2, 55.4, 47.8, 46.8, 46.0, 25.1, 11.9 ppm. MS (m/z, rel. int.): 534 (M$^+$, 0.3), 409 (6), 397 (20), 369 (100), 193 (24), 165 (88). Analysis Calculated for C$_{26}$H$_{23}$ClN$_6$OS$_2$ (535.0938 g/mol)

|  | % C | % H | % N |
|---|---|---|---|
| Calculated | 58.36 | 4.33 | 15.71 |
| Found | 58.45 | 4.40 | 15.69 |

EXAMPLE 2

The Neuroprotective Effect of LA U-8080 on Bright Light-Treated Photoreceptors.

The light-induced retina damage model selectively promotes the killing of photoreceptor cells as it occurs in age-related macular degeneration and retinitis pigmentosa.

Sprague-Dawley rats (150–175 g males) were dark adapted for 3 days. Two hours before light treatment they were injected i.p. with LAU-8080 (30 mg/kg) suspended in a vehicle (cyclo-dextrin) or just vehicle. A third group received no injection. Rats were placed in 5 inch diameter cylindrical lucite tubes which were then placed within an 8-light array of 10 inch diameter fluorescent lights (40 Watt, G.E. cool white; 350 µE/m$^2$·s; 25 klux) for up to 5 hours. After 10 days in darkness, eyes were collected and prepared for histology. One micron-thick plastic sections were examined and photoreceptor nuclei observed from the superior edge, through the optic nerve, to the inferior edge of the retina. The profile of the photoreceptor nuclear layer of the light+vehicle, light+vehicle+LAU-8080, and dark rat retinas were compared. The percent cell loss under each condition was calculated against the dark animal controls.

Normal, healthy rat retinas have a photoreceptor nuclear layer that is 12 nuclei deep. When 4 hours of light treatment occurs, 30% of the photoreceptor nuclei are lost. The majority of these are localized in the central upper half of the retina. However, while light causes severe cell loss, the same amount of light treatment has little or no effect when the animal is pretreated with LAU-8080; in an area near the center of the photodamage region, the complete lack of cell loss was noted. The photoreceptor nuclear layer remained 12 cells deep. FIG. 1 is a graphic representation of these treatments. Each curve is the average of 5 animal retinas. As shown in FIG. 1, light+vehicle shows the greatest cell loss (30%), while light+vehicle+LAU-8080 shows only 5% cell loss when compared to the dark retinas (n=43).

Four-hour constant bright light will cause about 30% of the photoreceptors to be lost after 10 days. (This is actually slightly more than 50% when considering only the upper retina). Vehicle alone has no effect on this loss of photoreceptors, but LAU-8080 almost totally protects the photoreceptors from light damage, with a maximum cell loss of 5% across the entire retina.

LAU-8080 can be used to slow down the loss of sight in age-related macular degeneration (ARMD) and retinitis pigmentosa (RP). In these diseases photoreceptor cells die. In both ARMD and RP common photoreceptor events may lead to cell death and LAU-8080 can slow down those pathological events and therefore limit blindness.

The use of this compound will be either by injection (intramuscular) or orally in a tablet form, per os. The compound can be administered during prolonged periods of time after the disease onset is apparent.

EXAMPLE 3

LA U-8080 Inhibits In Vivo Angiogenesis in the Eye.

The mouse corneal micropocket assay according to the procedure of B. M. Kenyon et al., "A model of angiogenesis in the mouse cornea," Invest. Ophthalmol. Vis. Sci. vol. 37, pp. 1625–1632 (1996), was used to test whether LAU-8080 would inhibit angiogenesis.

Mouse corneal micropocket assay: Corneal micropockets were created with a modified von Graefe knife in both eyes of 5- to 6-weeks old mice. Pellets containing vehicle of 0.1% BSA in PBS with 12% polyhydroxyethylmetacrylate (Hydron) were implanted in the corneas at 1 mm from the limbus of the mice for a control. For the PAF experiment, 500 ng cPAF was added to the pellet with vehicle. For the PAF-LAU experiment, mice were implanted with Hydron pellets containing 0.1% BSA in PBS, 500 ng CPAF, and then treated with the PAF antagonist LAU-8080 (30 $\mu$g/g body weight), i.p., once a day. Six days later, corneal pictures were taken under the microscope and vessel length and clock hours of circumferential neovascularization were measured.

Figure 2:
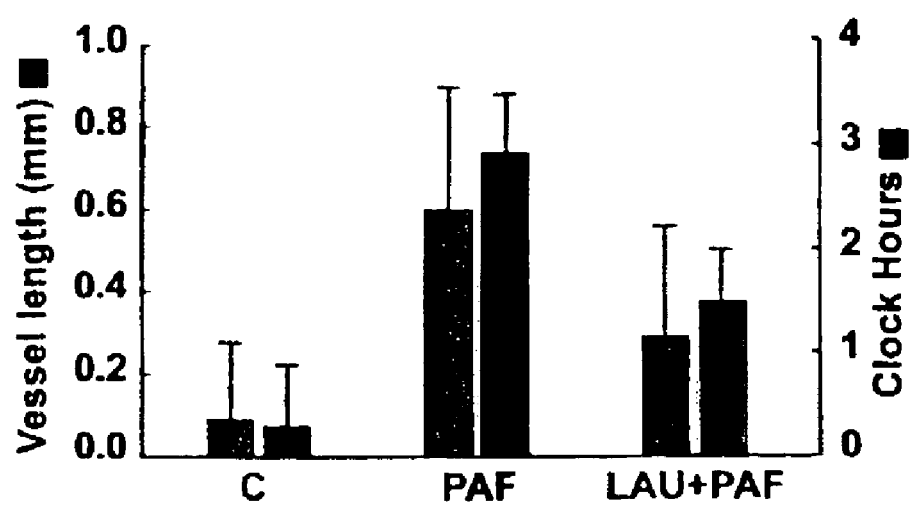
FIG. 2 illustrates the change in angiogenesis in a mouse cornea when implanted with a control vehicle, with platelet activating factor (PAF), and with PAF and LAU-8080 (LAU+PAF).

At 6 days, after implantation of the pellets, angiogenesis was strongly induced by PAF in mice corneas (p, 0.0001 for both vessel length and clock hours). See FIG. 2. However, angiogenesis was significantly reduced in the animals treated with the PAF antagonist LAU-8080 (p<0.05).

Thus, LAU-8080 was shown to inhibit angiogenesis in the mouse cornea. LAU-8080 in either injectable (intramuscular) or in a tablet form, per os, can be used to help prevent or retard age-related macular degeneration, retinitis pigmentosa, and diabetic retinopathy. The use of this compound will be administration for prolonged periods of time after the disease onset to slow down photoreceptor cell death and to inhibit pathological neovascularization.

EXAMPLE 4

Neuroprotection by LA U-8080 in Stroke.

In stroke, neurons typically die due to the shortage of blood as well as to the reperfusion-induced damage. Using an animal model of stroke, LAU-8080 was injected one hour after the stroke. As described below, the use of LAU-8080 resulted in enhanced survival, improved clinical recovery, and decreased the size of the brain lesion.

To study the properties of LAU-8080 in an animal model of stroke, the technique of occluding the middle cerebral artery (middle cerebral artery occlusion, "MCAO") which has been adapted to the mouse was used. The mouse middle cerebral artery occlusion is a well-recognized model of focal stroke as neuronal damage occurs when ischemia-reperfusion damages the brain. Adult male mice (C57BL/6) weighing 22–25 grams were induced to anesthesia with 1/70/30% halothane/nitrous oxide/oxygen, on a temperature controlled blanket. A line of PAF-R deficient mice (PAF receptor Knock-out mice), as described in S. Ishi et al., "Impaired anaphylactic responses with intact sensitivity to endotoxin in mice lacking a platelet-activating factor," J. Exp. Med., vol. 187, pp. 1779–1788 (1998), was also used.

The common carotid and external carotid arteries were exposed and dissected from surrounding tissue; the right external carotid artery was ligated. The right common carotid was temporarily occluded. A small arteriotomy to the external carotid artery was made so the occluding filament was introduced and advanced to the common carotid artery, and redirected into the internal carotid artery. The filament was advanced so that the blunted tip was placed in the anterior cerebral artery and the side of the filament occluded the origin of the middle cerebral artery. The common carotid artery was gently released, restoring blood flow to the carotid system. The wound was inspected for bleeding. All retracting sutures were removed, and the wound was closed. The anesthetic gases were stopped, and the animal was given oxygen until fully awake, then returned to his cage. After 60 minutes of occlusion, animals were reperfused by removal occluding filament. Animals were placed under anesthesia again, the occluding suture was delicately withdrawn from the arterial lumen, restoring blood flow to the territory of the middle cerebral artery. The wound was closed by interrupted silk sutures. The anesthetic gases were stopped, and the animal was given oxygen until fully awake.

The treated animals received a single i.p. injection of LAU-8080 (30 mg/kg) at 1 hour after reperfusion started, and control animals received vehicle injection (2-hydroxypropyl-$\beta$-cyclodextrin).

For purposes of measuring neurological deficits, caused by MCAO and reperfusion, animals were observed in their spontaneous movements, or induced by tail-pinching, after recovery from anesthesia and each 24 hours thereafter. Scores were collected according Bederson's classification: a score of "0" indicates the animal moved freely changing directions. A score of "1" indicates the animal showed difficulties to extend the left forepaw. A score of "2" indicates the animal had difficulties with both left forepaw and hind paw, i.e., the animal had the tendency to run or move in circles usually to the left. A score of "3" indicates serious coordination movements, the animal after stimulation kept rolling over. Finally "4" indicates the animal could not move even after stimulation.

Volumetric changes in infarcted brain regions in mice after 1 hour MCAO and 24–48 hours reperfusion was obtained by staining brain slices 1 mm thick with 2% 2,3,5-triphenyltetrazolium chloride (TTC). Quantitative analysis of the volume of the infarcted area was obtained by image-analysis.

Figure 3:
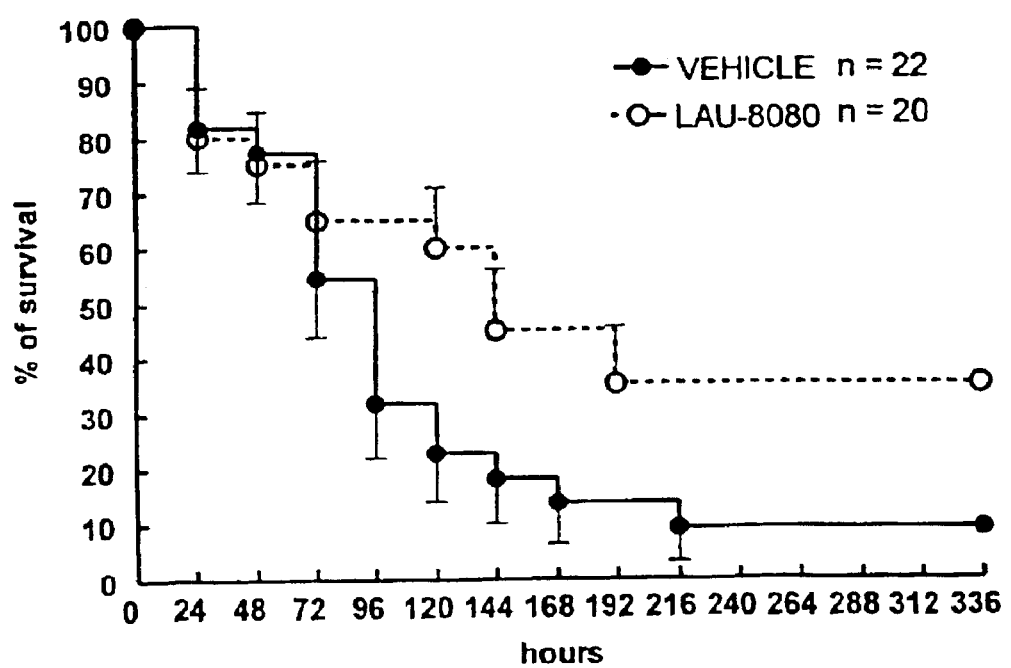
FIG. 3 illustrates the increase in percent mouse survival after a stroke was simulated by middle cerebral artery occlusion and reperfusion, and then treated with LAU-8080 as compared to treatment with a control vehicle.

This study indicated that treatment with the specific intracellular PAF receptor antagonist LAU-8080 reduced infarct volumes in the middle cerebral artery territory, and promoted better recovery from stroke in animals after MCAO. In animals receiving 1 hour MCAO and an injection of LAU-8080 one hour after the onset of reperfusion, survival curves showed a significant increase as compared with with vehicle treated animals (35% survival on LAU-8080, 8% on vehicle, p<0.04 n=20 and 22 respectively). See FIG. 3. The study was followed-up for 14 days after reperfusion started.

Figure 4:
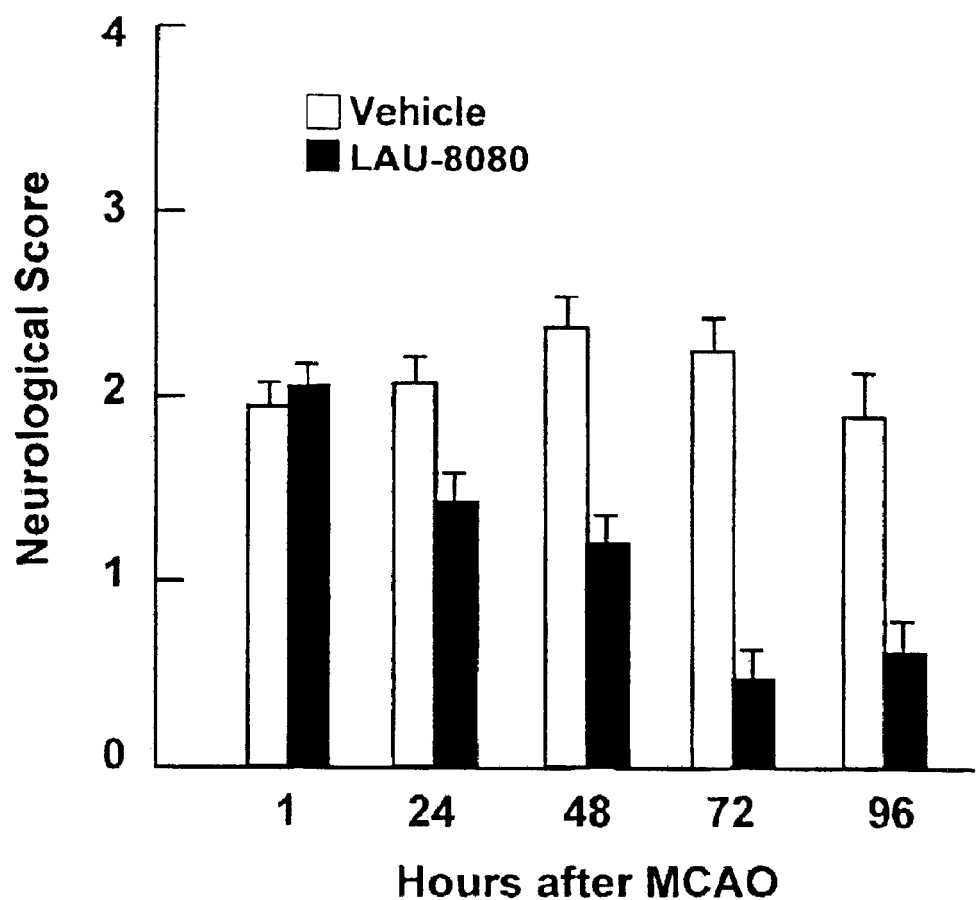
FIG. 4 illustrates the decrease in neurological deficits in mice after a stroke was simulated by middle cerebral artery occlusion and reperfusion, and then treated with LAU-8080 as compared to treatment with a control vehicle.

Neurological scores indicated a significative improvement on animals treated with LAU-8080; recovery was noticeable already 24 hours after reperfusion. See FIG. 4.

Figure 5:
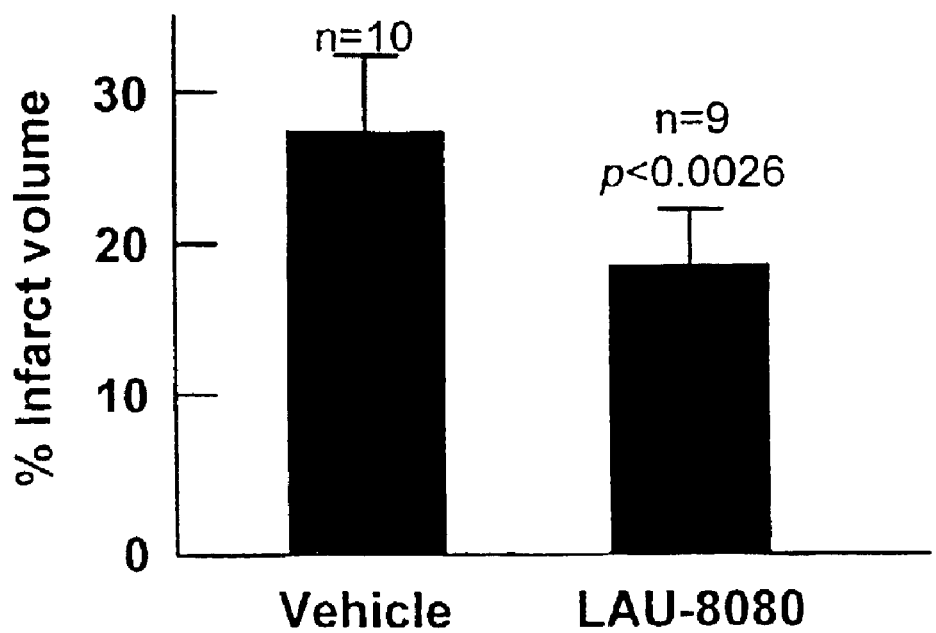
FIG. 5 illustrates the reduction in infarct volume in mice after a stroke was simulated by middle cerebral artery occlusion and reperfusion, and then treated with LAU-8080 as compared to treatment with a control vehicle.

Infarct volume studies on animals after 1 hour of MCAO and 48 hours reperfusion with injection of LAU-8080 at 1 hour after reperfusion onset indicated a significant reduction of the infarcted volume on the treated animals (p<0.0026). See FIG. 5.

In the PAF receptor deficient mice (PAF receptor Knock-out mice), a small reduction in infarct volume was seen with LAU-8080. The PAF receptor Knock-out mice lack the surface receptors for PAF, but still have intracellular PAF receptors. Thus, these results confirm that LAU-8080 acts as an antagonist to the intracellular PAF receptors.

Figure 6:
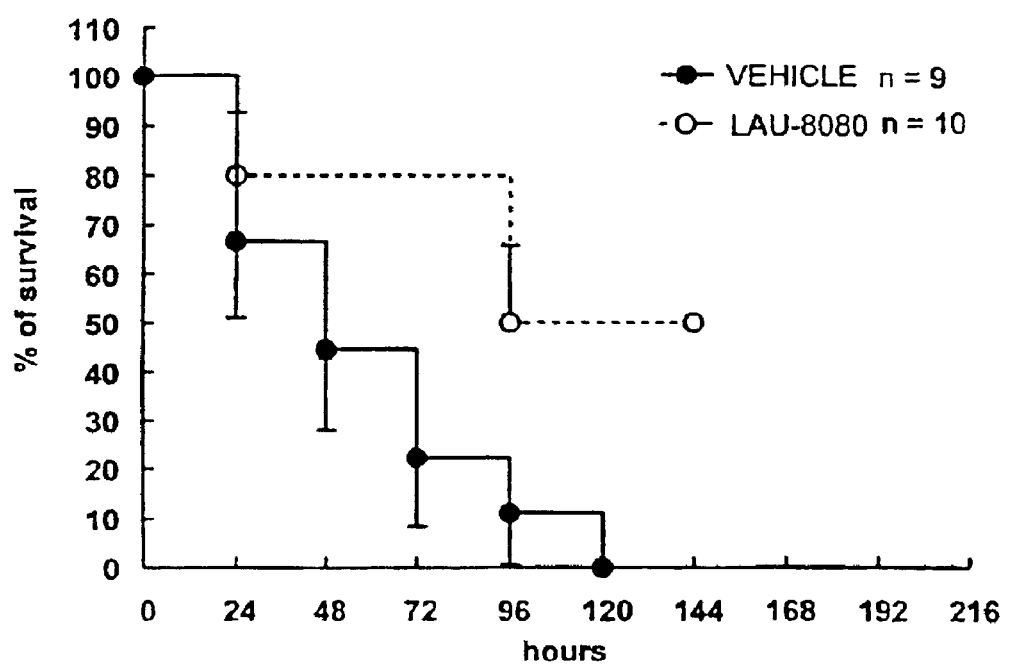
FIG. 6 illustrates the increase in percent mouse survival in PAF knock-out mice after a stroke was simulated by middle cerebral artery occlusion and reperfusion, and then treated with LAU-8080 as compared to treatment with a control vehicle.

When survival studies were performed with injection of LAU-8080 one hour after reperfusion, a significative protection was obtained (p<0.0074) See FIG. 6.

The use of LAU-8080 injection at different times during the procedure did not differ significantly from the animals treated 1 hour after reperfusion. This indicated the applicability of this drug within the time window necessary in most clinical conditions of stroke. This study demonstrates the suitability of the use of LAU-8080 as a therapeutic agent to prevent further brain damage.

Thus LAU-8080 can be used therapeutically after a stroke to minimize the loss of neurons due to the ischemia-reperfusion damage. The route of administration will be by either intramuscular or intravenous injection.

Literature Cited:
(1) Doucet J P, Bazan N G: Excitable membranes, lipid messengers, and immediate-early genes: Alteration of signal transduction in neuromodulation and neurotrauma. Mol Neurobiol 6(4):407–424, 1992.
(2) Bazan H E P, Tao Y, Bazan N G: Platelet-activating factor induces collagenase expression in corneal epithelial cells. Proc Natl Acad Sci 90:8678–8682, 1993.
(3) Kato K, Clark G D, Bazan N G, Zorumski C F: Platelet activating factor as a potential retrograde messenger in $Ca^1$ hippocampal long-term potentiation. Nature 367:175–179, 1994.
(4) Marcheselli V L, Bazan N G: Platelet-activating factor is a messenger in the electroconvulsive shock-induced transcriptional activation of c-fos and zif-268 in hippocampus. J Neurosci Res 37:54–61, 1994.
(5) Bazan N G, Fletcher B S, Herschman H R, Mukherjee P K: Platelet-activating factor and retinoic acid synergistically activate the inducible prostaglandin synthase gene. Proc Natl Acad Sci 91:5252–5256, 1994.
(6) Jerusalinsky D, Fin C, Quillfelot J A, Beatriz C F, Schmitz P K, Da Silva R C, Walz R, Bazan N G, Medina J H, Izquierdo I: Effect of antagonists of platelet-activating factor receptors on memory of inhibitory avoidance in rats. Behav and Neural Biol 62:1–3, 1994.
(7) Bazan N G: Signals, messages and genes in cerebral ischemia: Novel sites for neuroprotection. In: *Pharmacology of Cerebral Ischemia* 1994. J Krieglstein, H Oberpichler-Schwenk (eds.), Wissenschaftliche Verlagsgesellschaft mbH Stuttgart, pp. 3–15, 1994.
(8) Bazan N G, Allan G: Phospholipid degradation, second messengers and activation of cell signaling genes. In: *Cell Signal Transduction, Second Messengers, and Protein Phosphorylation in Health and Disease.* A M Municio and M T Miras-Portugal (eds.), Plenum Press, New York, pp. 95–100, 1994.
(9) Tao Y, Bazan H E P, Bazan N G: Platelet-activating factor induces the expression of metalloproteinases-1 and -9 but not -2 or -3 in the corneal epithelium. Invest Ophthalmol Vis Sci 36(2):345–354, 1995.
(10) Izquierdo I, Fin C, Schmitz P K, Da Silva R C, Jerusalinsky D, Quillfeldt J A, Ferreira M B G, Medina J H, Bazan N G: Memory enhancement by intrahippocampal, intraamygdala, or intraentorhinal infusion of platelet-activating factor measured in an inhibitory avoidance task. Proc Natl Acad Sci USA 92:5047–5051, 1995.
(11) Bazan N G, Marcheselli V L, Mukhexjee P K: Inducible prostaglandin synthase in cell injury. In: *Advances in Prostaglandin, Thromboxane, and Leukotriene Research,* Vol 23, B Samuelsson et al., (eds.) Raven Press, New York, pps. 317–323, 1995.
(12) Bazan N G, Rodriguez de Turco E B, Allan G: Mediators of injury in neurotrauma: Intracellular signal transduction and gene expression. J Neurotrauma 12(5) :791–814, 1995.
(13) Bazan N G: Regulation of the inducible prostaglandin synthase gene and second messengers in brain: Implications for stroke. In: *Cerebrovascular Diseases,* Nineteenth Princeton Stroke Conference, Chapter 20, M A Moskowitz and L R Caplan (eds), Butterworth-Heinemann, Newton, Mass., pp 231–250, 1995.
(14) Bazan N G, Allan G, Marcheselli V L: An inhibitor of injury-induced COX-2 transcriptional activation elicits neuroprotection in a brain damage model. In: *Improved Non-Steroid Anti-Inflammatory Drugs: COX-2 Enzyme Inhibitors.* Sir J Vane, J Botting and R Botting (eds.), Kluwer Academic Publishers, Lancester, United Kingdom, 9:145–166, 1996.
(15) Bazan N G, Kolko M, Allan G: Excitable membrane-derived lipid mediators: Glutamate release and regulation of gene expression. In: *Neurodegenerative Diseases: Molecular and Cellular Mechanisms and Therapeutic Advances,* G Fiskum (ed.), Plenum Publishing Corporation, New York, pps 409–425, 1996.
(16) Bazan N G, Allan G: Platelet-activating factor is both a modulator of synaptic function and a mediator of cerebral injury and inflammation. In: *Advances in Neurology, Vol. 71:Cellular and Molecular Mechanisms of Ischemic Brain Damage.* B Siesjö and T Wieloch (eds.), Lippincott-Raven Publishers, Philadelphia, 37:475–484, 1996.
(17) Bazan N G, Marcheselli V L, Allan G, van Meter K, Moises J P: Brain COX-2 in experimental models of epilepsy and stroke: Signaling pathways leading to enhanced expression. In: *New Targets in Inflammation-:Inhibitors of COX-2 or Adhesion Molecules,* N G Bazan, J Botting, J R Vane (eds.), William Harvey Press and Kluwer Academic Publishers, United Kingdom, 1996.
(18) Marcheselli V L, Bazan N G: Sustained induction of prostaglandin endoperoxide synthase-2 by seizures in hippocampus: Inhibition by a platelet-activating factor antagonist. J Biol Chem 271:24794–24799, 1996.
(19) Tao Y, Bazan H E P, Bazan N G: Platelet-activating factor enhances urokinase-type plasminogen activator (uPA) gene expression in corneal epithelium. Invest Ophthalmol Vis Sci 37:2037–2046, 1996.
(20) Bazan N G and Allan G: Platelet activating factor in the modulation of excitatory amino acid neurotransmitter release and of gene expression. J Lipid Mediat Cell Signal 14:321–330, 1996.
(21) Bazan N G: Inflammatory signaling pathways in pharmacology of cerebral ischemia. In: *Pharmacology of Cerebral Ischemia.* J Krieglstein, Medpharm Scientific Publ, Stuttgart, pp 173–180, 1996.
(22) Bazan N G, Allan G: Signal transduction and gene expression in eye:A contemporary view of the pro-inflammatory, anti-inflammatory and modulatory roles of prostaglandins and other bioactive lipids. Surv Ophthalmol 41 [Suppl 2]:S23–S34, 1997.
(23) Bazan N G. Lipid messengers and prostaglandin endoperoxide synthase-2 in neuronal cell death. In: *Primer Cerebrovascular Diseases.* M Welsh, L Chaplan, D Reis, B Siesjö, B Weir (eds), Academic Press, pps. 1322–1326, 1997.
(24) Bazan N G: Synaptic messengers, inflammatory mediators, and neuronal plasticity in cerebral ischemia.

In: *Maturation Phenomenon in Cerebral Ischemia II, Neuronal Recovery and Plasticity,* U Ito, T. Kirino, T. Kuroiwa, I. Klatzo (eds), Springer-Verlag Berlin Heidelberg. pps 19–25, 1997.

(25) Bazan N G, Marcheselli V L, Mukherjee P K, Lukiw W J, Gordon W C, Zhang D: COX-2 in brain and retina: Role in neuronal survival. In: *Selective COX-2 Inhibitors, Pharmacology, Clinical Effects and Therapeutic Potential.* J Vane, J Botting (eds), Chapter 4, Kluwer Academic Publishers and William Harvey Press, London, UK, pp. 47–53, 1997.

(26) Bazan H E P, Tao Y, DeCoster M A, Bazan N G: Platelet-activating factor induces cyclooxygenase-2 gene expression in corneal epithelium. Requirement of calcium in the signal transduction pathway. Invest Ophthalmol Vis Sci 38:2492–2501, 1997.

(27) Bazan N G and Allan G: Platelet-activating factor and other bioactive lipids. In: *Cerebrovascular Disease, Pathophysiology, Diagnosis and Management.* M D Ginsberg, J Bogousslavsky (eds). Chapter 37, Blackwell Science Publishers, Maiden, Mass., pps. 532–555, 1998.

(28) DeCoster M A, Mukherjee P K, Davis R J, Bazan N G: Platelet-activating factor is a downstream messenger of kainate-induced activation of mitogen-activated protein kinases in primary hippocampal neurons. J Neurosci Res 53:297–303, 1998.

(29) Teather L A, Packard M G, Bazan N G: Effects of posttraining intrahippocampal injections of platelet-activating factor and PAF antagonists on memory. Neurobiol of Learning and Memory 70:349–63, 1998.

(30) Bazan N G: Bioactive lipids and gene expression in neuronal plasticity. Adv Exp Med Biol 446:37–49, 1998.

(31) Mukherjee P K, DeCoster M A, Campbell F Z, Davis R J, Bazan N G: Glutamate receptor signaling interplay modulates stress-sensitive mitogen-activated protein kinases and neuronal cell death. J Biol Chem 274:6493–6498, 1999.

(32) Bazan N G; The inflammatory mediator platelet-activating factor and the inducible prostaglandin synthase (COX-2) gene in CNS diseases. In: *Inflammatory Cells and Mediators in CNS Diseases.* Ruffolo et al (eds), Harwood Academic Publishers, Amsterdam, The Netherlands, pp. 245–255, 1999.

(33) Serou M, DeCoster M A, Bazan N G: Interleukin-1 beta activates expression of cyclooxygenase-2 and inducible nitric oxide synthase in priamry hippocampal neuronal culture: Platelet-activating factor as a preferential mediator of cyclooxygenase-2 expression. J Neurosci Res 58:593–598, 1999.

(34) Marcheselli V L, Bazan N G: A specific antagonist for intracellular platelet-activating factor (PAF) binding sites lacks activity on synaptic membranes. Trans Amer Soc Neurochem 22:187, 1991.

(35) Bazan N G, Doucet J P: Phospholipase $A_2$ activation, platelet-activating factor, and expression of cell-signaling genes. Phospholipids and Signal Transduction Conference, May 29–Jun. 2, 1991, Wiesbaden, Germany.

(36) Bazan N G, Marcheselli V L, Doucet J, Allan G: Phospholipid degradation, second messengers, and activation of cell-signaling genes. Satellite Meeting of the 13th International Society for Neurochemistry "Neurobiology of Essential Fatty Acids," Jul. 10–12, 1991, Cairns, Australia.

(37) Bazan N G: Neuronal cell signal transduction and gene expression in response to injury and experimental epilepsy. Fifth International Symposium MSNR 91, "New Frontiers in the Biochemistry and Biophysics of Stroke, Neurotrauma and Other Neurological Disorders," Sep. 1–8, 1991, Bristol, England.

(38) Doucet J P, Marcheselli V L, Bazan N G: Triazolobenzodiazepine-based antagonism of platelet-activating factor and induction of fos expression in human SH-SY5Y neuroblastoma cells. Soc Neurosci 17:170, 1991.

(39) Feuerstein G Z, Bazan N G, Piomelli D, Bliss T V P: Symposium, ALipid Mediators in Synaptic Transduction of Neuronal Cells: Physiological and Pathological Implications. Soc Neurosci 17:1470, 1991.

(40) Marcheselli V L, Doucet J P, Bazan N G: Platelet-activating factor is a mediator of fos expression induced by a single seizure in rat hippocampus. Soc Neurosci 17:349, 1991.

(41) Marcheselli V L, Bazan N G: ECS-induced zif-268 in hippocampus is inhibited by a PAF antagonist. Trans Amer Soc Neurochem 23:255, 1992.

(42) Bazan N G: The role of lipid second messengers in brain injury. International Symposium on Pharmacology of Cerebral Ischemia, Jul. 20–22, 1992, Marburg, Germany.

(43) Bazan N G, Doucet J P: Immediate-early genomic response to PAF in NG108-15 neurohybrid cells in sensitive to an intracellular PAF antagonist. Fourth International Congress on PAF and Related Lipid Mediators, Snowbird, Utah, Sep. 22–25, 1992.

(44) Bazan N G, Doucet J P: Signal transduction and transcription modulation by lipid second messengers. Ocular Cell and Molecular Biology Symposium, Dallas, Tex., Oct. 17–18, 1992.

(45) Mukherjee P K, Bazan N G: Cell specific activation of zif/268 promotor by platelet-activating facto in transfected NG108-15 and SH-SYSY cells. FASEB J 7(4):A470, 1993.

(46) Doucet J P, Bazan N G: Muscarinic induction of zif/268 immediate-early gene in NG108-15 cells in mediated by platelet-activating factor. FASEB J 7(4):A184, 1993.

(47) Marcheselli V L, Bazan N G: Platelet activating factor (PAF) enhances glutamic acid release in the retina through a presynaptic receptor. Suppl Invest Ophthalmol Vis Sci 34(4):1048, 1993.

(48) Bazan N G, Marcheselli V L, Mukherjee P K, Allan G: The platelet-activating factor intracellular signalling pathway couples stimulation with immediate-early gene expression. 14th Biennial Meeting of the International Society for Neurochemistry in Montpellier, France, Aug. 22–27, 1993.

(49) Bazan N G, Marcheselli V L: Synaptic and intracellular platelet-activating factor (PAF) binding sites in brain. 14th Biennial Meeting of the International Society for Neurochemistry in Montpellier, France, Aug. 22–27, 1993.

(50) Marcheselli V L, Bazan N G: Intracellular platelet-activating factor binding sites and immediate-early gene expression in hippocampus during seizures. Satellite of the 14th Meeting of the International Society for Neurochemistry in Montpellier, France, Aug. 28–Sep. 2, 1993.

(51) Bazan N G, Prouet P, Marcheselli V L: A PAF antagonist blocks PAF-induced glutamic acid release from dissociated retinal cells as well as from retinal synaptosomes. Soc Neurosci 23:1414, 1993.

(52) Marcheselli V L, Bazan N G: Platelet-activating factor (PAF) stimulates glutamic acid release from hippocampal synaptosomes. Soc Neurosci 23:1779, 1993.

(53) Marcheselli V L, Bazan N G: Platelet-activating factor presynaptic receptor activation induces glutamic acid release in the retina, a mechanism associated with retinal damage. The Thirty Third Annual Meeting of American Society of Cell Biology, New Orleans, La., Dec. 11–15, 1993.

(54) Bazan N G, Marcheselli V L, Mukherjee P: The platelet-activating factor intracellular signaling pathway couples stimulation with gene expression. Keystone Symposium on A Protein Kinase C: Regulation, Structure, Function and Role in Human Diseases in Taos, N. Mex., Feb. 26–Mar. 4, 1994.

(55) Marcheselli V L, Bazan N G: A PAF antagonist or dexamethasone inhibits the seizure-triggered sustained upregulation of the inducible prostaglandin synthase in the hippocampus. Soc for Neurosci 20:433.9, 1994.

(56) Lukiw W J, Marcheselli V L, Bazan N G: DNA-binding proteins at the promotor of the inducible TIS10/PGS-2 gene modified by seizures or ischemia in the hippocampus. Epilepsia 35(8):43, 1994.

(57) Marcheselli V L, Bazan N G: Sustained upregulation of inducible prostaglandin synthase expression in hippocampus by a single seizure: inhibition by a PAF antagonist. Epilepsia 35(8):138, 1994.

(58) Moises J, Allan G, Marcheselli V L, Mandhare V, Bazan N G: A PAF antagonist inhibits the expression of hippocampal immediate early genes in a kindling model of epilepsy. Epilepsia 35(8):139, 1994.

(59) Bazan N G: Platelet-activating factor is a synapse messenger and a modulator of gene expression. 26th Annual American Society for Neurochemistry, Mar. 5–9, 1995, Santa Monica, Calif.

(60) Bazan N G: Excitable membrane-derived injury mediators: Glutamate release and regulation of gene expression. XV Washington International Spring Symposium. Neurodegenerative Diseases >95: Molecular and Cellular Mechanisms, and Therapeutic Advances, Washington, D.C., May 15–17, 1995.

(61) Lukiw W J, Marcheselli V L, Mukherjee P K, Bazan N G: Protein-DNA interactions in the proximal promoter of the inducible cyclooxygenase (COX-2) gene in hippocampus during experimental epilepsy and brain damage. XV Washington International Spring Symposium. Neurodegenerative Diseases '95: Molecular and Cellular Mechanisms, and Therapeutic Advances, Washington, D.C., May 15–17, 1995.

(62) Bazan N G: Bioactive lipids in the modulation of excitatory amino acid neurotransmitter release and of gene expression. Satellite Meeting of 15th ISN, "Lipid Messengers in the Nervous System," Tokyo, Japan, Jun. 28–30, 1995.

(63) Bazan N G: Lipid-derived second messengers in the regulation of gene expression. The Advanced School of Neurochemistry 2nd Biennial Course on "From Signal Transduction to Gene Expression," Okazaki, Japan, Jun. 28–Jul. 2, 1995.

(64) Bazan N G: Phospholipase $A_2$ in neuronal plasticity. 15th ISN Biennial Meeting Symposium on "Phospholipases and Lipid Second Messengers in the Normal and Pathologic Brain," Kyoto, Japan. Jul. 2–7, 1995.

(65) Bazan N G: Platelet-activating factor in synaptic transmission. 15th ISN Biennial Meeting Workshop on "Phospholipases," Kyoto, Japan, Jul. 2–7, 1995.

(66) Bazan N G: Bioactive lipid and neuronal plasticity in neurodegenerative diseases. 655th Meeting of Biochemical Society, University of Manchester, Manchester, England, Jul. 18–21, 1995.

(67) Bazan N G: PAF modifies cell function and pathology by affecting gene expression. Fifth International Congress on Platelet-activating Factor and Related Lipid Mediators. Berlin, Germany, Sep. 12–16, 1995.

(68) Lukiw W J, Marcheselli V L, Mukherjee P K, Bazan N G: Protein-DNA interactions in the promoter of the cyclooxygenase (COX2) primary response element in NG 108-15 cells in rat and human brain. Soc Neurosci 21:830, 1995.

(69) Marcheselli V L, Bazan N G: Inducible prostaglandin synthase and zif-268 mRNA upregulation in vasogenic cerebral edema: Inhibition by a PAF antagonist. Soc Neurosci 21:1867, 1995.

(70) Mukherjee P, DeCoster M A, Bazan N G: Platelet-activating factor is a messenger in kainate epileptogenesis-enhanced mitogen activated protein kinase activity in hippocampus. Soc Neurosci 21:1475, 1995.

(71) Mukherjee P, DeCoster M A, Bazan N G: Kainic acid-induced epileptogenesis increases mitogen activated protein kinase activity in hippocampus: Involvement of platelet-activating factor as a mediator. Epilepsia 36(S4):26, 1995.

(72) Bazan N G, Marcheselli V L: Seizure-induced lasting transcriptional upregulation of prostaglandin H synthase-2 (COX-2) in hippocampus: Inhibition by a platelet-activating factor antagonist. American Society for Neurochemistry, Mar. 2–6, 1996.

(73) Bazan N G, Marcheselli V L, Moises J: Synaptic messengers, inflammatory mediators, and neuronal plasticity. The Second International Workshop on Maturation Phenomenon in Cerebral Ischemia-Neuronal Recovery and Plasticity, Tokyo, Japan, Mar. 31–Apr. 1, 1996.

(74) Gordon W C, Marcheselli V L, Bazan N G: Retinal COX-2 induction by light preceeds photoreceptor cell death. International Symposium on New Targets in Inflammation: Inhibitors of COX-2 or Adhesion Molecules, New Orleans, La., Apr. 15–16, 1996.

(75) Lukiw W J, Marcheselli V L, Bazan N G: Human COX-2 promoter modulators. International Symposium on New Targets in Inflammation: Inhibitors of COX-2 or Adhesion Molecules, New Orleans, La., Apr. 15–16, 1996.

(76) Marcheselli V L, Bazan N G: Transcriptional upregulation of COX-2 in hippocampus by seizures. International Symposium on New Targets in Inflammation: Inhibitors of COX-2 or Adhesion Molecules, New Orleans, La., Apr. 15–16, 1996.

(77) Mukherjee P, Dixon D, Prescott S, Smith D, Lukiw W, Bazan N G: PAF induction of human COX-2 gene. International Symposium on New Targets in Inflammation: Inhibitors of COX-2 or Adhesion Molecules, New Orleans, La., Apr. 15–16, 1996.

(78) Tao Y, Bazan HEP, Decoster MA, Bazan N G: COX-2 gene expression and $Ca^{2+}$ influx in corneal epithelial cells. International Symposium on New Targets in Inflammation: Inhibitors of COX-2 or Adhesion Molecules, New Orleans, La., Apr. 15–16, 1996.

(79) Bazan N G, Marcheselli V L, Rodriguez de Turco EB, Gordon WC. The early response gene cyclooxygenase-2 (COX-2) is selectively induced in rat retina at the onset of light damage. Suppl Invest Ophthalmol Vis 37:S1122, 1996.

(80) Bazan N G. Cinar N H, Marcheselli V L: Lipid second messengers and the upregulation of inducibe prostalandin synthase-2 triggered by vasogenic cerebral edema. The Joint Meeting of the American Society for Biochemistry and Molecular Biology, New Orleans, La., Jun. 2–6, 1996.

(81) Decoster Mass., Bazan N G: Platelet-activating factor modulates intracellular calcium dynamics in rat hippocampal neurons. The Joint Meeting of the American Society for Biochemistry and Molecular Biology, New Orleans, La., Jun. 2–6, 1996.

(82) Marcheselli V L, Gordon W C, Cinar N H, Beuckmann C T, Urade Y, Hayaishi O, Bazan N G: Prostaglanin D synthase is rapidly translocated from the retinal pigment epithelium into the interphotorecptor matrix, vitreous, and aqueous humor. The Joint Meeting of the American Society for Biochemistry and Molecular Biology, New Orleans, La., Jun. 2–6, 1996.

(83) Rodriguez de Turco E B, Marcheselli V L, Gordon W C, Bazan N G: The onset of light damage selectively induces the early response gene inducible cyclooxygenase in the rat retina. The Joint Meeting of the American Society for Biochemistry and Molecular Biology, New Orleans, La., Jun. 2–6, 1996.

(84) Tao Y, Bazan HEP, Decoster MA. Bazan N G: PAF induces cyclooxygenase (COX-2) gene expression in the corneal epithelium partially by a receptor-mediated calcium influx. The Joint Meeting of the American Society for Biochemistry and Molecular Biology, New Orleans, La., Jun. 2–6, 1996.

(85) Bazan N G: Inflammatory signalling pathways in pharmacology of cerebral ischemia. 6th International; Symposium on Pharmacology of Cerebral Ischemia, Marburg, Germany, Jul. 22–24, 1996.

(86) Bazan N G, Marcheselli V L, Gordon W C: The inducible prostaglandin synthase, an inflammatory response gene, is upregulated in the retina at the onset of light-triggered photoreceptor apoptosis. XII International Congress of Eye Research, Yokohama, Japan, Sep. 29–Oct. 4, 1996.

(87) Bazan N G: The inflammatory mediator platelet-activating factor and the inducible prostaglandin synthase (COX) gene in CNS disease. SmithKline Beecham Pharmaceutical Symposium, Collegeville, Pa., Nov. 14, 1996.

(88) Baker M L, Gebhardt B M, Bazan N G: Differential effect of platelet-activating factor on adhesion molecule expression by astrocytes and microglia. Soc Neurosci 22:1796, 1996.

(89) Marcheselli V I, Cinar H N. Stellingworth M A, Bazan N G: Seizures promote a rapid transcriptional upregulation of PGHS-2 in rat hippocampus, which inhibited by the PAF receptor antagonist BN 50730. Soc Neurosci 22:1439, 1996.

(90) Bazan N G: PAF is a transcriptional activator of PGH synthase-2: Significance for neuronal survival after injury. 1997 Keystone Symposia Conference on Lipid Mediators: Recent Advances in Molecular Biology, Understanding of Regulation and Pharmacology, Keystone, Colo., Jan. 26–31, 1997.

(91) Bazan N G: Injury messengers. transcription factors, and gene expression in status epilepticus. International Symposium on Status Epilepticus Mechanisms and Management, Santa Monica, Calif., Feb. 6–8, 1997.

(92) Bazan N G: COX-2 in the brain and retina: Role in neuronal survival. 12th William Harvey Reserch Conference, "Selective COX-2 inhibitors: Pharmacology, Clinical Effects and Therapeutic Potential", Cannes, France, Mar. 20–21, 1997.

(93) Bazan N G, Marcheselli V L, Gordon W C, Harris T, Zhang D: Increased upregulation of the inducible prostaglandin synthase (COX-2) gene precedes light-induced photoreceptor apoptosis. Experimental Biology, New Orleans, La., Apr. 6–9, 1997.

(94) Marcheselli V L, Campbell F, DeCoster M A, Bazan N G: Platelet-activating factor (PAF), kainic or glutamate increase expression of the inducible prostaglandin H synthase-2 (COX-2) in primary hippocampal neurons. Experimental Biology, New Orleans, La., Apr. 6–9, 1997.

(95) Mukherjee P K, DeCoster M A, Davis R J, Bazan N G: Differential activation of p38, JNK, and mitogen-activated protein kinases (MAPKs) by platelet-activating factor (PAF), glutamate (GLU), and kainate (KA) in primary hippocampal neurons. Experimental Biology, New Orleans, La., Apr. 6–9, 1997.

(96) Bazan N G, Marcheselli V L, Gordon WC: Prostaglandin endoperoxide synthase-2 (COX-2) overexpression is an early event in light-induced rod photoreceptor cell apoptosis. Suppl Invest Ophthalmol Vis Sci 38:S719, 1997.

(97) Harris T, Gordon W C, Marcheselli V L, Rodriguez EB, Bazan N G: Light-induced prostaglandin endoperoxide synthase-2 (COX-2) expression is selectively concentrated in inner segments of rod photoreceptors. Suppl Invest Ophthalmol Vis Sci 38:S1028, 1997.

(98) Mukherjee P K, Shima D T, Ng Y S, D'Amore P A, Bazan N G: Platelet-activating factor (PAF) induces the expression of vascular endothelial growth factor (VEGF). Suppl Invest Ophthalmol Vis Sci 38:S357, 1997.

(99) Bazan N G, Marcheselli V L, DeCoster M A, Ogden F, Lukiw W: Inflammatory messengers and COX-2 in neuronal cell death and alzheimer's disease (AD). Satellite of the Joint meeting of the 16th Biennial meeting of the International Society for Neurochemistry and the 28th Annual Meeting of the American Society for Neurochemistry, "8th International Symposium on Stroke, Neurotrauma and Other Neurological Diseases," New Orleans, La., Jul. 9–13, 1997. Biennial meeting of the International Society for Neurochemistry and the 28th Annual Meeting of the American Society for Neurochemistry, "8th International Symposium on Stroke, Neurotrauma and Other Neurological Diseases," New Orleans, La., Jul. 9–13, 1997.

(100) Mukherjee P K, DeCoster M A, Davis R J, Bazan N G: Platelet-activating factor (PAF) or kainate (KA) activation of P-38, JNK-1, and mitogen-activated protein kinases (MAPKs) follow different pathways than glutamate (GLU) in primary hippocampal neurons. Satellite of the Joint meeting of the 16th Biennial meeting of the International Society for Neurochemistry and the 28th Annual Meeting of the American Society for Neurochemistry, "8th International Symposium on Stroke, Neurotrauma and Other Neurological Diseases," New Orleans, La., Jul. 9–13, 1997.

(101) Bazan N G: Lipid messengers in synaptic signaling: significance in neuronal survival. Satellite of the Joint meeting of the 16th Biennial meeting of the International Society for Neurochemistry and the 28th Annual Meeting of the American Society for Neurochemistry, "Lipid Messengers in the Nervous System," New Orleans, La., Jul. 27–30, 1997.

(102) Campbell F Z, DeCoster M A, Marcheselli V L, Bazan N G: Excitatory amino acid neurotransmitter receptor agonists and platelet-activating factor (PAF) enhance the expression of the inducible prostaglandin synthase-2 (COX-2) in primary hippocampal neurons. Satellite of the Joint meeting of the 16th Biennial meeting of the International Society for Neurochemistry and the 28th Annual Meeting of the American Society for Neurochemistry, "Lipid Messengers in the Nervous System," New Orleans, La., Jul. 27–30, 1997.

(103) Marcheselli V L, Gordon W, Bazan N G: Significance of COX-2 in neuronal and photoreceptor survival. Satellite of the Joint meeting of the 16th Biennial meeting of the International Society for Neurochemistry and the 28th Annual Meeting of the American Society for Neurochemistry, "Lipid Messengers in the Nervous System," New Orleans, La., Jul. 27–30, 1997.

(104) Mukherjee P K, DeCoster M A, Davis R J, Bazan N G: Platelet-activating factor (PAF) or kainate (KA) activation of p-38, JNK-1, and mitogen-activated protein kinase (MAPKs) follow different pathways than glutamate (GLU) in primary hippocampal neurons. Satellite of the Joint meeting of the 16th Biennial meeting of the International Society for Neurochemistry and the 28th Annual Meeting of the American Society for Neurochemistry. "Lipid Messengers in the Nervous System," New Orleans, La., Jul. 27–30, 1997.

(105) Serou M, Marcheselli V L, DeCoster M A, Bazan N G: A secretory phospholipase $A_2$ ($sPLA_2$) receptor agonist induces expression of prostaglandin endoperoxide synthase-2 (COX-2) in primary cortical neurons but not glial cultures. Satellite of the Joint meeting of the 16th Biennial meeting of the International Society for Neurochemistry and the 28th Annual Meeting of the American Society for Neurochemistry, "Lipid Messengers in the Nervous System," New Orleans, La., Jul. 27–30, 1997.

(106) Teather L A, Packard M G, Bazan N G: Effects of intrahippocampal injections of platelet-activating factor and the PAF antagonists BN 52021 and BN 50730 on spatial memory in rats. Satellite of the Joint meeting of the 16th Biennial meeting of the International Society for Neurochemistry and the 28th Annual Meeting of the American Society for Neurochemistry, "Lipid Messengers in the Nervous System," New Orleans, La., Jul. 27–30, 1997.

(107) Bazan N G: COX-2 in synaptic plasticity and neurodegenerative diseases. First International Workshop on COX-2, New Orleans, La., Sep. 13–14, 1997.

(108) Bazan N G: PAF signal transduction and COX-2 expression: Significance in neuronal survival and in neurodegenerative diseases. Fifth International Conference on Eicosanoids and other Bioactive Lipids in Cancer, Inflammation and Related Diseases, La Jolla, Calif., Sep. 17–20, 1997.

(109) Bazan N G: The neuromessenger platelet-activating factor in plasticity and neurodegeneration. Satellite Symposium of the 27th Annual meeting of the Society for Neuroscience, on "Nitric Oxide and Other Diffusible Signals in Brain and Development, Plasticity, and Disease," New Orleans, La., Oct. 24–15, 1997.

(110) Bazan N G: Synaptic signaling to genes in epilepsy. $13^{th}$ Annual meeting of American Academy of Clinical Neurophysiology, New Orleans, La., Jan. 29–31, 1998.

(111) Bazan N G: Neuroprotection by controlling bioactive lipid signaling. American Society for Neurochemistry, Denver, Colo., Mar. 7–11, 1998.

(112) Bazan N G: Epileptogenesis: Significance of informationa flow, sprouting and neuronal damage. Merritt-Putnam, Lectures on Epilepsy, New Orleans, La., Apr. 18, 1998.

(113) Teather L A, Smith D E, Marcheselli V L, Bazan N G: Immunocytochemical localization of cyclooxygenase-2 (COX-2) in rat brain following kainic acid-induced status epilepticus. FASEB J 12:A750, 1998.

(114) Bazan N G: Endogenous neuroprotection mechanisms and inflammatory signaling in stroke. Princeton Conference, May 7–10, 1998.

(115) La Motta I, Hardy M, Allan G, Marcheselli V L, Bazan N G: Effect of overexpression of platelet-activating factor acetylhydrolase alpha subunit in light damaged photoreceptor cells. University of New Orleans, Howard Hughes Internship Research Day, New Orleans, La., May 8, 1998.

(116) Casey D, Marcheselli V L, Hardy M, Bazan N G: Light damage increased levels of PGHS-2 are prevented by overexpression of PAF acetylhydrolase. University of New Orleans, Howard Hughes Internship Research Day, New Orleans, La., May 8, 1998.

(117) Marcheselli V L, Bazan N G, Gordon W C: Enhanced expression of the inducible prostaglandin synthase gene precedes light-induced photoreceptor apoptosis. Second Annual Vision Research Conference on "Retinal Development, Degeneration and Function Restitution," Fort Lauderdale, Fla., May 8–9, 1998.

(118) Bazan N G: Bioactive lipids in synaptic signaling to genes. $12^{th}$ International Meeting of the European Society for Neurochemistry, St. Petersburg, Russia, Jul. 19–24, 1998.

(119) Bazan N G: COX-2 in ischemic brain injury and in neurodegeneration. Second International Workshop on COX-2, Kapalua, Hi., Jul. 28–31, 1998.

(120) Bazan N G: COX-2 in synaptic plasticity and neurodegeneration. IBCs Industry Symposium on COX-2 Inhibitiors, San Diego, Calif., Aug. 6–7, 1998.

(121) Bazan N G: Synaptic signaling, stress-sensitive protein kinases, and COX-2 in neuronal injury. Cambridge Healthtech Institute's, Acute Neuronal Injury: New Therapeutic Opportunities, Las Vegas, Nev., Sep. 23–24, 1998.

(122) Bazan N G: COX-2 and oxidative stress in ischemic brain injury and neurodegeneration. 5th IUBMB Conference on The Biochemistry of Health and Diseases, Jerusalem, Israel, Oct. 18–22, 1998.

(123) Wang, J-H, Li W, Marcheselli V L, Bazan N G, Sun G Y: Inhibition of cytokine action of PAF antagonists in immortalized astrocytes. Soc. Neurosci 28:1540, 1998.

(124) Bazan N G: Cell signaling and gene expression in photoreceptor survival. Keystone Symposia, Ocular Cell and Molecular Biology Symposium, Keystone, Colo., Feb. 5–10, 1999.

(125) Bazan N G: Stress sensitive signaling, synaptic activity and gene expression in neuronal survival. J Neurochem 72:S90A, 1999.

(126) Marcheselli V L, Bazan N G: Light damage induced photoreceptor apoptosis involves a PAF receptor mediated signaling pathway which involves upregulation of COX-2 and BCL-2. J Neurochem 72(S):S50D, 1999.

(127) Marcheselli V L, Bazan N G: Light damage induced photoreceptor apoptosis involves a PAF receptor mediated signaling pathway which involves upregulation of COX-2 and BCL-2. J Neurochem 72(S):S50D, 1999.

(128) Bazan N G: Synaptic activation, stress sensitive signaling and COX-2 expression in the brain. Association Pour la Neuro Psycho Pharmacologie, "Expression and Action of Anti-Inflammatory Cytokines in the Brain", Arachon, France, May 29–30, 1999.

(129) Bazan N G: Synaptic signaling in ischemia: Stress sensitive protein kinases, gene expression and neuronal survival. Minisymposium on Stroke, Kuopio, Finland, Jun. 10–11, 1999.

(130) Bazan N G: St. Charles Pharmaceutical, Inc.—A Start-Up Company. American Chemical Society, Younger Chemist Committee, "Trends in Biotechnology", New Orleans, La., Aug. 24–25, 1999.

(131) Moises J P, Marcheselli V L, Bazan N G: Brain injury induces COX-2 expression: Inhibition by a PAF antagonist. $17^{th}$ Annual National Neurotrauma Society meeting, Oct. 22–23, 1999.

(132) Bazan N G: Synaptic signaling, gene expression and neuronal survival. The 4$^{th}$ International Workshop, "Maturation Phenomenon in Cerebral Ischemia Apoptosis and/or Necrosis, Neuronal Recovery vs. Death, and Protection for Infarction, Oct. 30–Nov. 2, 1999.

(133) Marcheselli V L, Moises J P, Tian X H, Bazan N G: Partial inhibition of ischemia-reperfusion induced COX-2 gene expression is associated with neuroprotection in a model of MCAO. The 4$^{th}$ International Workshop, "Maturation Phenomenon in Cerebral Ischemia Apoptosis and/or Necrosis, Neuronal Recovery vs. Death, and Protection for Infarction, Oct. 30–Nov. 2, 1999.

(134) Gershanik E F, Gordon W C, Bazan N G: Antagonist of the intracellular platelet-activating factor (PAF) receptor protects photoreceptors from light damage. Suppl Invest Ophthalmol Vis Sci 41:S332, 2000.

The complete disclosures of all references cited in this specification are hereby incorporated by reference. Also incorporated by reference is E. F. Gershanik, W. C. Gordon, and N. G. Bazan, "Antagonist of the Intracellular Platelet-activating Factor (PAF) Receptor Protects Photoreceptors from Light Damage," IOVS Abstract Issue, vol. 41 (4), Mar. 8, 2000, for presentation at the ARVO 2000 Annual Meeting, Fort Lauderdale, Fla., Apr. 30–May 5, 2000. In the event of an otherwise irreconcilable conflict, however, the present specification shall control.

What is claimed:

1. A method of ameliorating, in a mammal, the pathological neovascularization of diabetic retinopathy in a patient, comprising administering to the mammal a therapeutically effective amount of LAU-8080.

* * * * *

UNITED STATES PATENT AND TRADEMARK OFFICE
CERTIFICATE OF CORRECTION

PATENT NO. : 6,987,105 B2
APPLICATION NO. : 10/258343
DATED : January 17, 2006
INVENTOR(S) : Nicolas G. Bazan et al.

Page 1 of 1

It is certified that error appears in the above-identified patent and that said Letters Patent is hereby corrected as shown below:

On the cover page at (75), inventor delete "Nicholas" and insert --Nicolas--.

Column 1, line 8, insert:

--The development of this invention was partially funded by the Government under Grant Nos. DEY005121 & NS023002 from the National Institutes of Health. The Government has certain rights in this invention.--

Signed and Sealed this

Twenty-third Day of September, 2008

JON W. DUDAS
*Director of the United States Patent and Trademark Office*